(12) United States Patent
Lim et al.

(10) Patent No.: US 7,544,356 B2
(45) Date of Patent: Jun. 9, 2009

(54) COMPOSITION FOR THE IMPROVEMENT OF LIVER FUNCTION, THE REDUCTION OF SERUM ETHANOL LEVEL AND ANTIOXIDANT ACTIVITY ENHANCEMENT

(75) Inventors: Kwang Sei Lim, Suwon-si (KR); Young Tae Ahn, Suwon-si (KR); Yong Hee Kim, Seoul (KR); Jin Seong Bae, Seongnam-si (KR); Ho Kyung Oh, Yongin-si (KR); Chul Sung Huh, Cheonan-si (KR)

(73) Assignee: Korea Yakult Co., Ltd., Seoul (KR)

( * ) Notice: Subject to any disclaimer, the term of this patent is extended or adjusted under 35 U.S.C. 154(b) by 238 days.

(21) Appl. No.: 11/406,970

(22) Filed: Apr. 19, 2006

(65) Prior Publication Data

US 2006/0233774 A1 Oct. 19, 2006

(30) Foreign Application Priority Data

Apr. 19, 2005 (KR) .................... 10-2005-0032417

(51) Int. Cl.
- *A01N 63/00* (2006.01)
- *A01N 63/02* (2006.01)
- *A23C 9/123* (2006.01)
- *A23C 23/00* (2006.01)
- *A23L 2/00* (2006.01)

(52) U.S. Cl. .............. 424/93.45; 426/61; 426/71; 426/590

(58) Field of Classification Search ............ None
See application file for complete search history.

(56) References Cited

U.S. PATENT DOCUMENTS

| | | | | |
|---|---|---|---|---|
| 5,989,556 A * | 11/1999 | Tsai et al. | ........... | 424/741 |
| 6,156,355 A * | 12/2000 | Shields et al. | ........... | 426/74 |
| 6,166,003 A * | 12/2000 | Lam | ........... | 514/183 |
| 6,241,983 B1 * | 6/2001 | Paul et al. | ........... | 424/93.4 |
| 6,329,002 B1 * | 12/2001 | Kim et al. | ........... | 426/71 |
| 6,843,994 B2 * | 1/2005 | Iwasaki | ........... | 424/195.15 |
| 7,234,931 B2 * | 6/2007 | Lee | ........... | 424/725 |
| 7,238,373 B2 * | 7/2007 | Meyrowitz | ........... | 424/655 |

* cited by examiner

*Primary Examiner*—Vera Afremova
(74) *Attorney, Agent, or Firm*—Birch, Stewart, Kolasch & Birch, LLP

(57) ABSTRACT

The present invention is directed to a composition for use in liver function improvement, blood alcohol level reduction and in-vivo antioxidant activity enhancement, comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, vitamin $B_1$, $B_2$, $B_3$, $B_6$, $B_9$, $B_{12}$, C, and E. The composition can improve declined liver functions and shows excellent hepatoprotective and hepatocurative activity against alcohol on excessive or habitual drinking with the ability to reduce blood alcohol levels. Its superior enhancement of in-vivo antioxidant activity also contributes to the use of the composition in the prevention of liver diseases and the improvement of liver functions. Also disclosed are fermented dairy foods, beverages, and health foods, containing the composition as an effective component.

12 Claims, 7 Drawing Sheets

COMPOSITION FOR THE IMPROVEMENT OF LIVER FUNCTION, THE REDUCTION OF SERUM ETHANOL LEVEL AND ANTIOXIDANT ACTIVITY ENHANCEMENT

FIELD OF THE INVENTION

The present invention relates to a composition that is useful for liver function improvement, blood alcohol level reduction, and in-vivo antioxidant activity. More particularly, the present invention relates to a composition which can improve decreased liver function and shows excellent hepatoprotective and hepatocurative activity caused by excessive or habitual drinking. In addition, the composition has with the ability to reduce blood alcohol levels in addition to having superior in-vivo antioxidant activity enhancement properties, thereby contributing to the prevention of liver diseases and the improvement of liver function. The composition comprises *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C and E.

BACKGROUND OF THE INVENTION

Oxygen is the most common element in the world, amounting to 53.8% of the total amount of all elements, and occupying about 21% of dry air. Most animals take in oxygen in order to acquire energy. Oxygen, although absolutely necessary for the life of almost all living beings, can be fatal present above toxicity levels. These Janus-like properties of oxygen depend on its molecular states. Ground state triplet oxygen, which is the most stable oxygen molecule, is responsible for the maintenance of life. Converted from the stable oxygen molecule by various physical, chemical and environmental factors, including enzymatic systems, reductive metabolism, chemicals, pollutants, photochemical reactions, etc., reactive oxygen species (ROS), a kind of highly reactive free radicals, such as superoxide radicals, $(O_2)$, hydroxyl radicals (HO), hydrogen peroxide $(H_2O_2)$, and singlet oxygen $(\frac{1}{2}O_2)$, causes serious diseases in the body. For example, ROS are likely to react with and destroy cellular constituents, such as lipids, proteins, sugars, nucleic acids, causing aging and various diseases including brain diseases, such as apoplexy, Parkinson's disease, etc., cardiovascular diseases, such as heart diseases, ischemia, arteriosclerosis, etc., dermal diseases, inflammation, rheumatism, and autoimmune diseases. Also, upon lipid peroxidation, lipid peroxides are accumulated to cause the oxidative destruction of cells, causing cells to malfunction. Particularly, the intake of oxidative chemicals, such as drugs, poisons, alcohols, etc., causes oxidation in the body, injuring the liver, and in severe cases, can lead to cirrhosis of the liver.

The liver is the largest internal organ in the body and plays a major role in metabolism. It has a number of functions in the body including drug detoxification, glycogen storage, and plasma protein synthesis. Also, as much as about 90% of blood proteins are produced in the liver. In addition, the liver functions to detoxify toxic chemicals and acts as an immune organ. Various drugs and hazardous materials are converted into less hazardous ones, which are secreted out of the body through urine or bile. Particularly, Kupffer cells, specialized macrophages located in the liver, function to remove from the blood any particulate contaminants that happen to be present, such as bacteria, toxins, or foreign substances.

The liver has the remarkable capacity to completely regenerate after injury. In fact, even after up to 75% partial hepatectomy, the liver restores its full functionality and size within 4-6 months.

However, the responsibility of the liver for such various and important functions also suggests that when the liver is not healthy, many significant problems occur.

According to the pathogenic cause, liver diseases may be divided: viral liver diseases are caused due to viral infection, alcoholic liver diseases due to excessive alcohol intake, toxic liver diseases due to drugs, steatic hepatitis due to fat accumulation, autoimmune liver diseases due to the abnormality of the immune system, and metabolic liver diseases due to the excessive accumulation of toxic materials.

One of the most rampant chronic liver diseases is caused by hepatitis B virus while hepatitis C intends to be widely spread. In addition, the outbreak of alcohol-induced liver diseases, although lower than that of viral liver diseases, has been significantly increased with habitual drinking.

Alcoholic liver diseases are largely classified into steatosis, alcoholic hepatitis and alcoholic cirrhosis according to clinicopathologic finding. Alcoholic steatosis is found in 90-100% of habitual drinkers. It is also known that between 10% and 35% and between 8% and 20% of habitual drinkers have alcoholic hepatitis and alcoholic cirrhosis, respectively.

Alcohol is absorbed mainly in the digestive tract, and 90% of the absorbed alcohol is metabolized in the liver while the remaining 10% is discharged via expiration, urine and perspiration. Alcohol, after being transported along with blood, is oxidized to acetaldehyde by various liver enzymes, such as alcohol dehydrogenase, a microsomal ethanol oxidizing system, catalase, etc., which is further enzymatically oxidized to acetic acid, which is harmless to the body. Meanwhile, alcohol is readily metabolized to acetaldehyde by enteric microorganisms. Recently, lactic acid bacteria in the intestine have been reported to convert ethanol into acetaldehyde and further to acetic acid, thereby suppressing the absorption of alcohol and acetaldehyde, with the concomitant hepatoprotective activity. However, not all lactic acid bacteria have such a function. Therefore, there is a need for developing the lactic acid bacteria that functions to prevent the absorption of alcohol and acetaldehyde and protect the liver. It is important that the lactic acid bacteria to be developed settle and multiply in the intestine. Particularly, lactic acid bacteria to be developed for use in humans must originate from humans because of their high host-specificity.

Acetaldehyde, a toxic product resulting from the breakdown of alcohol by alcohol dehydrogenase, is marked as a main factor causing liver damage. This metabolite of alcohol is highly reactive enough to readily associate with proteins, thereby decreasing enzyme activity. Also, acetaldehyde stimulates hepatic lipid peroxidation, which leads to damage to hepatic mitochondria and the depletion of glutathione, pyridoxine, vitamin A, zinc, and selenium, and determines a decrease in the ability of purified tubulin to polymerize, inhibiting protein secretion and transport. In addition, the production of free radicals by acetaldehyde activates the synthesis of collagen and is reported to cause liver fibrogenesis (cirrhosis) in habitual drinkers.

Hepatoprotective compositions or products comprising suppressing or stimulating agents of alcohol metabolism or alcohol dehydrogenases have been developed and commercialized. For example, a medicinal composition with hepatoprotective activity and liver disease-curing activity is disclosed in Korean Pat. No. 0178696, an herbal medicinal beverage for curing hangovers and improving liver functions and the preparation thereof in Korean Laid-Open Publication No. 2001-0050333, a functional food for curing hangovers and the preparation thereof using a mixed extract from the Japanese raisin tree, the Alder tree, and arrowroot in Korean Pat. No. 0345798, an agent for enhancing alcohol metabolism and relieving abnormal liver function in Korean Laid-Open Publication No. 2002-0021980, a hangover-curing and hepatoprotective composition comprising an alcohol absorption inhibitor in Korean Pat. Laid-Open Publication No. 2002-0004193, and a health food based on extracts from a Japanese raisin tree and an Alder tree in Korean Pat. Laid-Open Publication No. 2003-0005127.

In addition, a lower alcohol-insoluble extract from young Korean raisin tree stems, a polysaccharide material prepared there from, and a composition containing the same with the activity of relieving hepatotoxicity, hangover, and fatigue are disclosed in Korean Pat. No. 0403720; a lower alcohol-insoluble extract fraction from Japanese raisin trees, a polysaccharide material prepared there from, and a composition containing the same and having activity of relieving hepatotoxicity and hangovers in Korean Pat. No. 0403721; a lower alcohol-insoluble extract from the xylem of Korean raisin trees, a polysaccharide prepared there from, and a composition containing the same and having hepatoprotective activity in Korean Pat. No. 0403722; and a hangover-curing agent and a composition based on the same in Korean Pat. Laid-Open Publication No. 2004-0052930. All of these patents aim to cure hangovers occurring upon excessive drinking rather than to protect or improve liver function as a precautionary measure.

Thus far, nowhere has been mentioned a composition having hepatostimulant, hepatoprotective and hepatogenerative activity, based on *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C and E.

SUMMARY OF THE INVENTION

Therefore, it is an object of the present invention to provide a composition that is useful for use in liver function improvement, blood alcohol level reduction and antioxidant activity enhancement in the human body.

It is another object of the present invention to provide a fermented dairy food useful in liver function improvement, blood alcohol level reduction and antioxidant activity enhancement in the human body, containing the composition as an effective component.

It is a further object of the present invention to provide a beverage food useful in liver function improvement, blood alcohol level reduction and antioxidant activity enhancement in the human body, containing the composition as an effective component.

It is still a further object of the present invention to provide a health food useful in liver function improvement, blood alcohol level reduction and antioxidant activity enhancement in the human body, containing the composition as an effective component.

The above objects could be achieved by a provision of a composition for liver function improvement, blood alcohol level reduction and in-vivo antioxidant activity enhancement, comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C and E.

In accordance with an aspect of the present invention, a fermented dairy food containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C, and E.

In accordance with another aspect of the present invention, a functional beverage, containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, vitamins $B_1$, $B_2$, $B_3$, $B_6$, $B_9$, $B_{12}$, C, and E, is provided.

In accordance with a further aspect of the present invention, a health food, containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C, and E, is provided.

BRIEF DESCRIPTION OF THE DRAWINGS

The application of the preferred embodiments of the present invention is best understood with reference to the accompanying drawings, in which like reference numerals are used for like and corresponding parts, wherein.

DETAILED DESCRIPTION OF THE INVENTION

Figure 1:
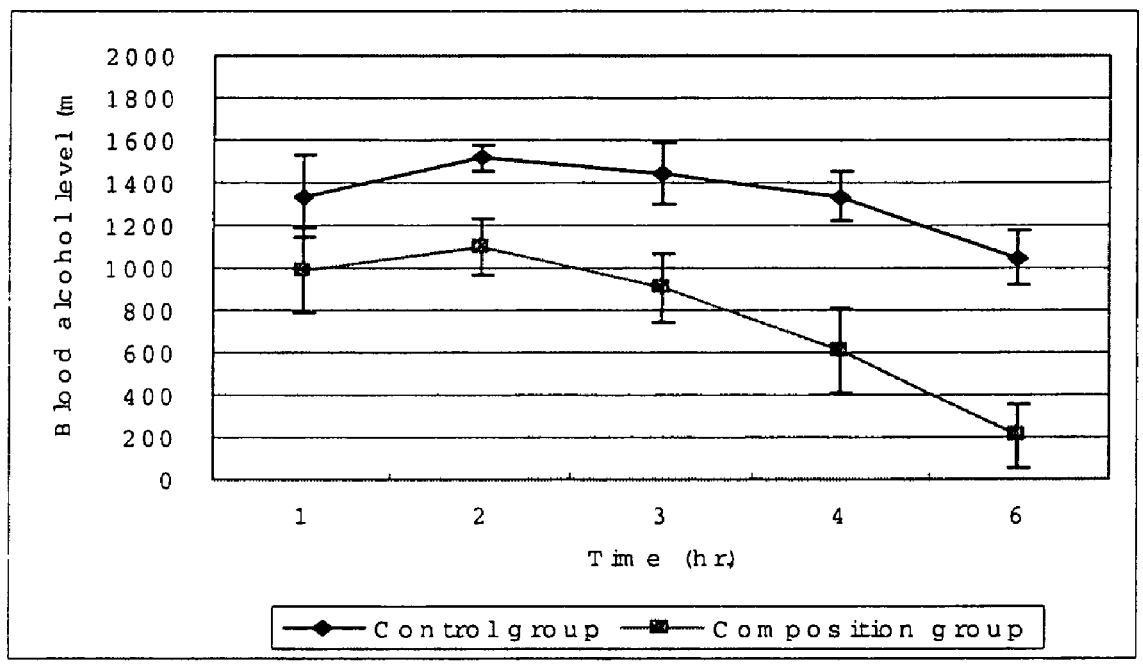
FIG. 1 is a graph showing the ability of the composition of the present invention to decrease blood alcohol levels in animal tests.

The present invention pertains to a composition that is useful for improving liver functions, reducing blood alcohol levels, and enhancing in-vivo antioxidant activity, comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, vitamins $B_1$, $B_2$, $B_3$, $B_6$, $B_9$, $B_{12}$, C and E.

*Lactobacillus brevis* HY7401, which was deposited in Korean Collection for Type Cultures (KCTC) with Accession No. KCTC 11314BP on Apr. 17, 2008 contained in the composition for use in improving liver functions, reducing blood alcohol levels, and enhancing in-vivo antioxidant activity, is a strain isolated from the feces of healthy Korean adults. Having high alcohol (ethanol) and acetaldehyde dehydrogenase activity, this strain can metabolize alcohol (ethanol) to acetaldehyde and further to acetic acid. Thus, because this strain can convert acetaldehyde, an agent injurious to the liver, into acetic acid, which is non-toxic to the liver, in the intestinal organs, it effectively prevents alcohol (ethanol) from being absorbed into the liver, thereby preventing the occurrence of disorders attributable to excessive alcohol metabolism, such as abnormalities in liver function, alcoholic liver diseases, and intestinal diseases.

As a constituent of the composition useful for improving liver functions, reducing blood alcohol levels, and enhancing in-vivo antioxidant activity, *Lactobacillus fermentum* CS332, which was deposited in Korean Collection for Type Cultures (KCTC) with Accession No. KCTC 11372BP on Jul. 31, 2008, is involved in alcohol (ethanol) metabolism in the small intestine so as to reduce the level of alcohol and acetaldehyde in blood. Thus, this bacteria functions to oxidize alcohol to non-toxic forms in the small intestine, thereby preventing the absorption of alcohol in the small intestine and reducing the burden of alcohol metabolism on the liver (Yang, W. Y., Ahn Y. T., Lim, K. S., Huh, C. S., Baek, Y. J., and Kim, H. S. 2004. Ethanol metabolism by probiotic lactic acid bacteria in-vivo. Proceeding of 2004 JOINT ANNUAL MEETING. American Dairy Science Association, American Society of Animal Science, Poultry Science Association. p. 384).

*Lactobacillus acidophilus* CSG which may be obtained form Culture systems, Inc. located at 3224 N. Home Street Mishawaka, Ind. 46545. Tel:(574) 428 0602/Fax:(574) 258 1136 and *Bifidobacterium longum* HY8001, which was deposited in Korean Culture Center of Microorganisms with Accession No. KCCM 10959P on Sep. 7, 1995 (Korean Pat. No. 142615), contained in a composition that is useful for improving liver functions, reducing blood alcohol levels, and enhancing in-vivo antioxidant activity, are found to have potential inhibitory activity against the hepatotoxicity of carbon tetrachloride in rats, with better ability to decrease the level of liver enzymes (AST and ALT) than that of commercially available liver drugs (HAN, Song Yi, HUH, Cheol Sung, KIM, Tong Hyun. Hepatoprotective effect of lactic acid bacteria, inhibitor of beta-glucuronidase production against intestinal bacteria. The Pharmaceutical Society of Korea, Fall Academic Symposium Proceeding. 2004).

A mixture comprising an Alder tree extract, a Selfheal extract, a milk thistle extract, a green bean-rice bran fermentation extract and a turnip extract, all contained in the composition useful for improving liver functions, reducing blood alcohol levels, and enhancing in vivo antioxidant activity, has hepatoprotective and alcohol degrading activity (termed Y-MIX, Korean Pat. Application No. 10-2004-0072213) and shows the following effects.

The Alder tree (*Alnus japonica* Steud.) is a tall larch tree belonging to the family Betulaceae and growing throughout Asia. However, it is written in the literature on herbal medicine that only trees native to Korea are useful in curing alcohol poisoning and protecting the liver. An extract from this tree is composed mainly of tannin, taraxerol, a kind of triterpenoid, betulinic acid, and essential oil. In herbal medicine, this tree is known as a pharmaceutical tree showing curative activity for various liver diseases, such as hepatitis, cirrhosis, fatty liver, etc.

In order to be used as an herbal medication, Selfheal (*Prunella vulgaris* var. *lilacina* Nakai) is gathered when half withered in the summer, and dried under the sun. In herbal medicine, this herbal medication is applied for the treatment of chronic tumors, smallpox, acute mastitis, and tuberculous lymphadenopathy. It was found to contain saponins such as oleanolic acid, ursolic acid, etc., carotine, vitamin C, vitamin K, tannin, caffeic acid, and chlorogenic acid as main components [Comprehensive Bibliography on Korean Useful Plant Resource, the Korea Research Institute of Chemical Technology pp. 480-482(1988)].

Milk thistles (*Silybum marianum* L. Gaertn.), belonging to the genus *Silybum* Adans., grow as annual or biennial plants native to the Mediterranean regions of Europe, North Africa and the Middle East, and have been widely used as medicinal herbs. This plant herb is known to give some remedy for liver diseases: liver poisoning, chronic inflammatory liver diseases, viral hepatitis and cirrhosis. Its potent extract responsible for the remedy is used in medicine under the name of silymarin. Another extract, silibinin, is used against poisoning. In addition, the extract from milk thistles is found to show various physiological activities, including the promotion of protein synthesis leading to liver regeneration, the inhibition of formation of leukotriene and inflammatory prostaglandin, potent antioxidation, and the prevention of depletion of glutathione, a component essential for detoxification after excessive drinking.

The green bean-rice bran fermentation extract used in the present invention is prepared by fermenting a mixture of green coffee beans and rice bran in the presence of microorganisms and extracting the fermented mixture and contains inositol phosphate and polyphenol, both functioning as antioxidants and reactive oxygen species scavengers, as well as amino acids and peptides. The green bean-rice bran fermentation extract can be commercially obtained from Toyo Hakko, which manufacturer is located at 1-39-1, Yoshikawacho, Obu-Shi, Aichi-Ken, 474-0046 Japan and telephone number is 81-562-46-7677 and facsimile number is 81-562-46-8122. With the antioxidation and toxic oxygen-scavenging function, the fermentation extract is helpful for preventing DNA damage (which may lead to cancer), the peroxidation of unsaturated fatty acids, and the hypertension attributed to ACE inhibition.

In turnips (*Brassica campestris* L. var. *rapifera*), there are sulfur-containing compounds including isothiocyanate, disulfide, and sulforaphane. Also, isocyanate, responsible for the hot taste of turnips, has long been known as an anticancer ingredient and has recently been proven to prevent esophageal cancer, liver cancer, lung cancer, and large intestinal cancer in animal tests. Also, recent studies with animals reported that turnip extract relieves conditions of liver cancer and cirrhosis.

A tomato extract, a broccoli extract and a pineapple extract, all contained in the composition useful for improving liver functions, reducing blood alcohol levels, and enhancing in-vivo antioxidant activity, may constitute an antioxidant composition (Korean Pat. Application No. 10-2005-0009441) and are described with respect to their properties below.

The tomato (*Lycopersicon esculentum* Mill) is a plant in the Solanaceae or Nightshade family, originating in the highlands on the west coast of South America. Its fruits are edible and have been used as folk remedies for hypertension, nightblindness and diabetes. The fruits are composed mainly of water (95 wt %), with 0.7 wt % of proteins, 0.1 wt % of lipids, 3.3 wt % of carbohydrates, 0.4 wt % of cellulose, and 0.5 wt % of ashes as minor constituents. 100 g of tomato fruits contains 390 μg of carotene, 20 mg of vitamin C, 0.05 mg of vitamin $B_1$, and 0.03 mg of vitamin $B_2$ in addition to vitamin $B_6$, potassium, phosphor, manganese, rutin, and niacin. Also, various physiologically active materials including lycopene, quercetin, phytoene, phytofluene, cycloycopene, salicylates, and tomatine are found in tomato fruits. Particularly, the tomato is known as a main source of lycopene, which is better in antioxidant capacity than carotenoid and vitamin E and shows good anticancer activity. It is reported that as much as 80% of the lycopene intake of Americans comes from tomatoes or their processed foodstuff. Quercetin, a kind of flavones, is known to inhibit the expression of the receptor of the male hormone androgen, and therefore shows a preventive effect on prostate cancer.

Broccoli (*Brassica oleracea* var. *italica* Plenck) is a plant of the cabbage family, also called cauliflower. Usually edible are young sprouts and stems thereof. Broccoli is one of the most nutritious green-yellow vegetable crops, with 114 mg vitamin C, 1.9 mg carotene, 164 mg potassium, and 150 mg calcium per 100 g broccoli. Also, broccoli contains more iron than do other vegetables ("twice as much iron as"=200%; "two times more iron than"=300%). Particularly, broccoli is rich in vitamin C, having a vitamin C content that is two times higher than that of lemon and seven times higher than that of potatoes. In addition, the level of minerals including vitamin A, $B_1$ and $B_2$, potassium, phosphorus, and calcium in broccoli is as high as that in spinach. Meanwhile, glucosinolate, which broccoli contains in abundance, has anticancer activity and is reported to be much more inhibitory of colon cancer than is cabbage. Particularly, recent research has disclosed that sulforaphane, a product of the enzymatic breakdown of glucosinolate of broccoli, selectively enhances the activity of glutathione S-transferase in-vivo, preventing cancer generation.

The pineapple (*Ananas comosus*), native to Central America and the North region of South America, is a dicotyledonous plant belonging to the family Bromeliaceae of the order Farinales, growing as a perennial plant. The fruit was named "pineapple" because of its resemblance to a pine cone, is highly juicy and tastes freshly sour and sweet with contents of 1% sucrose and 1% citric acid. The fruit is rich in vitamins A, B and C, with the highest content of vitamin C among all fruits, amounting to 60 mg per 100 g of pineapple. The pineapple contains bromelain, a protease, which is helpful for the digestion of meats and serves as an anticoagulant that works by breaking down the blood clotting proteins fibrin and fibrinogen.

Betaine (trimethylglycerine), contained in the composition useful for the improvement of liver function, the reduction of serum alcohol levels, and the enhancement of in-vivo antioxidant activity, functions very closely with choline, folic acid, and vitamin $B_{12}$. All of these compounds function as "methyl donors." They carry and donate methyl molecules to facilitate necessary biochemical processes. The donation of methyl groups by betaine is very important to proper liver function, cellular replication, and detoxification reactions. When alcohol is taken, the activity of methionine synthetase in hepatocytes becomes too low to methylate homocysteine, which is formed after methionine metabolism, resulting in the accumulation of the hepatotoxic compound homocysteine. Betaine reduces the level of homocysteine in the blood, and particularly improves alcohol-induced fatty liver. Foods rich in betaine include fish, sugar beets, and leguminous plants.

The colostrum powder, used as a constituent of the composition according to the present invention, is prepared by drying the colostrums from diary cattle and is found to contain a large quantity of immunoglobulins against the hepatitis A virus (Korean Pat. Application No. 10-2004-0072212).

Playing an important role in energy metabolism, the vitamin B family, thiamin ($B_1$), riboflavin ($B_2$), niacin ($B_3$), folic acid ($B_9$), and cobalamin ($B_{12}$), all contained in the composition useful for the improvement of liver functions, the reduction of blood alcohol levels, and the enhancement of in-vivo antioxidant activity, is involved in the conversion of nutrients of food into biological energy. When feeling physical or mental fatigue, the body consumes the vitamin B family, called the anti-stress vitamin, faster than any other nutrient. Human bodies need not only these vitamins in order to resist stress, but also are supplemented with the vitamins immediately after complete consumption due to stress. A deficiency of vitamin B may incur fatigue, anxiety, hair loss, and nail injury. Vitamin $B_6$, vitamin $B_{12}$, and folic acid work like betaine to conduct a hepatoprotective function by reducing the content of the hepatotoxic compound homocysteine in the blood.

Vitamin C, contained in the composition useful for the improvement of liver function, the reduction of blood alcohol content and the enhancement of in-vivo antioxidant activity, is an antioxidant and is water-soluble. Scorbutus is highly likely to occur upon the deficiency of vitamin C. Besides, vitamin C is reported to be preventive of cancer, schizophrenia, AIDS, and purpura. Functioning as an antioxidant, vitamin C readily loses and donates electrons to oxidized enzymes or compounds. Vitamin C is usually found in many fruits and vegetables.

Vitamin E, contained in the composition useful for the improvement of liver function, the reduction of blood alcohol content, and the enhancement of in-vivo antioxidant activity, is a fat-soluble vitamin that is an important antioxidant. Alpha-tocopherol is traditionally recognized as the most active form of vitamin E in humans, and is a powerful biological antioxidant. Individuals who are deficient in vitamin E may undergo a decrease in virility, muscle weakness, degeneration of central and peripheral nerves, generation of heart tumors, and erythrocytic membrane fragility. Anyone diagnosed with cystic fibrosis and individuals with malabsorptive problems such as Crohn's disease may not absorb fat, and should discuss the need for supplemental vitamin E with their physician. People who cannot absorb fat often pass greasy stools or have chronic diarrhea. Individuals with abetalipoproteinemia may be prescribed special vitamin E supplements by a physician to treat this disorder. In addition, there may occur abnormal beta-lipoproteinemic sera, chronic ticlopidine-induced cholestatic hepatitis, and infant steatorrhea upon vitamin E deficiency.

With the characteristics described above, *Lactobacillus brevis* HY7401, *Lactobacillus fermentum* CS332, *Lactobacillus acidophilus* CSG, *Bifidobacterium longum* HY8001, the Alder tree extract, the Selfheal extract, the milk thistle extract, the green bean-rice bran fermentation extract, the turnip extract, the tomato extract, the broccoli extract, the pineapple extract, the colostrum powder, betaine, vitamin $B_1$, $B_2$, $B_3$, $B_6$, $B_9$, and $B_{12}$, and vitamin C and E may be mixed in various ratios and, in terms of pharmaceutical effects including the improvement of liver function, the reduction of blood alcohol levels, and the enhancement of in-vivo antioxidant activity, and the production cost. In one embodiment *Lactobacillus brevis* HY7401 is contained in an amount from about 0.001% by weight to about 0.1% by weight, and preferably in an amount of about 0.01% by weight; *Lactobacillus fermentum* CS332 in an amount from about 0.001% by weight to about 0.1% by weight and preferably in an amount of about 0.01% by weight; *Lactobacillus acidophilus* CSG in an amount from about 0.001% by weight to about 0.1% by weight and preferably in an amount of about 0.01% by weight; *Bifidobacterium longum* HY8001 in an amount from about 0.001% by weight to about 0.1% by weight, and preferably in an amount of about 0.01% by weight; the Alder tree extract in an amount from about 32% to about 36% by weight and preferably in an amount of about 35% by weight; the Selfheal extract in an amount from about 38% to about 42% by weight and preferably in an amount of about 40% by weight; the milk thistle extract in an amount from about 0.1% to about 0.8% by weight and preferably in an amount of about 0.5% by weight; the green bean-rice bran fermentation extract in an amount from about 1% to about 2.5% by weight and preferably in an amount of about 2% by weight; the turnip extract in an amount from about 0.1% to about 0.2% by weight and preferably in an amount of about 0.16% by weight; the tomato extract in an amount from about 0.8% to about 1.5% by weight and preferably in an amount of about 1% by weight; the broccoli extract in an amount from about 0.1% to about 0.5% by weight and preferably in an amount of about 0.3% by weight; the pineapple extract in an amount from about 0.15% to about 0.25% by weight and preferably in an amount of about 0.2% by weight; the colostrum powder in an amount from about 3.0% to about 4.0% by weight and preferably in an amount of about 3.5% by weight; betaine in an amount from about 4.5% to about 5.0% by weight and preferably in an amount of about 4.8% by weight; a composite vitamin premix in an amount from about 2.0% to about 3.0% by weight and preferably in an amount of about 2.35% by weight; and water in an amount from about 3.85% to about 18.24% by weight and preferably in an amount of about 10% by weight, based on the total weight of the composition.

If *Lactobacillus brevis* HY7401, *Lactobacillus fermentum* CS332, *Lactobacillus acidophilus* CSG and *Bifidobacterium longum* HY8001 are each contained in an amount lower than about 0.001% by weight, it is difficult for them to colonize themselves in the human intestines. On the other hand, a content higher than about 0.1% by weight causes an increase in production cost. Thus, the content of each of *Lactobacillus brevis* HY7401, *Lactobacillus fermentum* CS332, *Lactobacillus acidophilus* CSG and *Bifidobacterium longum* HY8001 is preferably between 0.001% by weight to 0.1% by weight on the basis of total weight of the composition.

The Alder tree extract is preferably contained in an amount from about 32% to about 36% by weight based on the total weight of the composition of the present invention. If the content of the alder tree extract is below about 32% by weight of the composition, the ability to decrease the level of alcohol in blood is lowered. On the other hand, if the alder tree extract is present in an amount higher than about 36% by weight, the composition acquires a bad taste and turns black, in addition to increasing in production cost.

A Selfheal extract content lower than about 38% by weight may lower the antioxidant effect of the composition. On the other hand, if the content exceeds about 42% by weight, the composition acquires a bad taste and turns black, in addition to causing an increase in production cost. Thus, preferable is a content of the Selfheal extract between about 38% by weight and about 42% by weight, based on the total of the composition of the present invention.

If present in an amount lower than about 0.1% by weight, the milk thistle extract lowers an effect of liver function improvement and antioxidant activity enhancement to the composition. More than about 0.8% by weight of the milk thistle extract makes the composition taste bad and leads to an increase in production cost. Therefore, the milk thistle extract content is preferably between about 0.1% by weight and about 0.8% by weight, based on the total weight of the composition of the present invention.

Based on the total weight of the composition, the green bean-rice bran fermentation extract is preferably contained in an amount from about 1.0% to about 2.5% by weight. Less than about 1.0% by weight of the green bean-rice bran fermentation extract is too small to impart an antioxidant effect to the composition. On the other hand, the content, if exceeding about 2.5% by weight, results in increasing the production cost of the composition.

Preferably, the turnip extract content ranges from about 0.1% to about 0.2% by weight, based on the total weight of the composition. If not enough turnip extract is used, the composition may be ineffective for hepatocellular regeneration. On the other hand, if too much turnip extract is used, the production cost of the composition increases.

Also, the tomato extract preferably ranges in content from about 0.8% to about 1.5% by weight, based on the total weight of the composition of the present invention. Less than about 0.8% by weight of the tomato extract lowers the antioxidant activity of the composition. On the other hand, higher than about 1.5% by weight of the tomato extract induces an increase in production cost.

It is preferred that the broccoli extract be used in an amount from about 0.1% to about 0.5% by weight, based on the total weight of the composition of the present invention. Less than about 0.1% by weight lowers the antioxidant activity of the composition, while more than about 0.5% by weight increases the production cost.

It is also preferred that the pineapple extract be used in an amount from about 0.15% to about 0.25% by weight, based on the total weight of the composition of the present invention. When the pineapple extract is present in an amount less than about 0.15% by weight, it lowers the antioxidant activity of the composition. More than about 0.25% by weight of the pineapple extract increases the production cost of the compound.

Preferably, the content of the colostrum powder is between about 3.0% and about 4.0% by weight, based on the total weight of the composition of the present invention. If the colostrum powder is contained in an amount less than about 3.0% by weight, the composition is ineffective in defending against the hepatitis A virus. Higher than about 4.0% by weight of the colostrum powder also increases the production cost.

Betaine lowers the function of regenerating injured liver cells well if it is present in an amount less than about 4.5% by weight, and causes an increase in the production cost if used in an amount larger than about 5.0% by weight. Thus, the amount of betaine is preferably between about 4.5% and about 5.0% by weight, based on the total weight of the composition of the present invention.

The composite vitamin premix is preferably contained in an amount from about 2.0% to about 3.0% by weight on the basis of the total amount of the composition. If the composite vitamin premix is contained in an amount less than about 2.0% by weight, the composition becomes poor in hepatotoxic material removing capacity and antioxidant activity. On the other hand, the composition containing more than about 3.0% by weight of the composite vitamin premix tastes bad and increases the production cost.

A better understanding of the present invention may be given with the following examples which are set forth to illustrate, but are not to be construed to limit the present invention.

EXAMPLE 1

Preparation of the Composition for Use in Liver Function Improvement, Blood Alcohol Level Reduction and In-Vivo Antioxidant Activity Enhancement

*Lactobacillus brevis* HY7401 was cultured at 37° C. for about 16 hours in broth containing proteose peptone #3, yeast extract, beef extract, and glucose and the culture medium was centrifuged to harvest the bacteria which was then washed with sterilized physiological saline and suspended in sterile milk. Lyophilization of the suspension gave a freeze-dried powder containing about $10^{11}$ cfu per g.

*Lactobacillus fermentum* CS332 was also cultured in the same manner as *Lactobacillus brevis* HY7401, and a freeze-dried powder containing about $10^{11}$ cfu per g was obtained.

*Lactobacillus acidophilus* CSG was also cultured in the same manner as in *Lactobacillus brevis* HY7401 and a freeze-dried powder containing about $10^{11}$ cfu per g was obtained.

*Bifidobacterium longum* HY8001 was cultured in a broth containing proteose peptone #3, a yeast extract, a beef extract, glucose, and L-cystein and finally, a freeze-dried powder containing about $10^{11}$ cfu per g was prepared.

100 g of the xylem and bark of the dried Alder tree was put into 1000 g of water and boiled at 100° C. for about 1 to about 5 hours. The solution was filtered through a 5 μm filter to yield afford 500 g of an Alder tree extract.

50 g of dried Selfheal in 1000 g of water was boiled at 100° C. for 1~5 hours, followed by filtering the solution through a 400 mesh filter to produce 600 g of a Selfheal extract.

A milk thistle extract in a powder state was purchased (TGS, Japan), and had a total flavonoid content of 80% to 95% by weight and a sylibin content of about 28% to about 32% by weight. Also purchased were a green bean-rice bran fermentation extract in a liquid state (Toyo Hakko, Japan) and a turnip extract in a liquid state (34 to 36 Brix°) (KangHwa Product. Co. Ltd.).

Together with 100 g of water, 100 g of tomato fruit was ground using a mixer and the juice was filtered through a cotton cloth. 125 g of the tomato filtrate was spray-dried to produce about 4.5 g of a tomato extract.

100 g of parboiled broccoli pieces, along with 100 g of water, was ground using a mixer and allowed to stand for 2 hours. Filtration through a cotton cloth gave 100 g of a broccoli filtrate which was then lyophilized to produce about 1.8 g of a broccoli extract.

The pineapple extract was prepared by slicing 100 g of cold water-washed pineapple into small pieces, grinding the slices in the presence of 100 g of water using a mixer, filtering the mixture through a cotton cloth, and spray-drying 100 g of the filtrate. Finally, the pineapple extract was obtained in an amount of about 4.5 g.

As for the colostrum powder, it was purchased from Culture Systems Korea. When diluted 50,000-fold with distilled water, the colostrum powder showed a titer of the IgG specific for HAV (hepatitis A virus) in the range from about 1 to about 1.7 OD at 490 nm.

Commercially available betaine anhydrous having a purity of about 99% to about 100% by weight (DANISCO, Finland) was used in the composition.

A commercially available composite vitamin premix (DSM, Singapore) was used for the vitamin components of the composition. The composite vitamin premix contains about 0.6933% by weight thiamine hydrochloride ($B_1$), about 0.6312% by weight riboflavin ($B_2$), about 6.1265% by weight niacin amide ($B_3$), about 0.9982% by weight pyridoxine hydrochloride ($B_6$), about 0.1461% by weight folic acid ($B_9$), about 0.5065% by weight vitamin $B_{12}$, about 56.4972% by weight sodium ascorbate (vitamin C), about 25.1558% by weight vitamin E, and about 9.2452% by weight maltodextrin.

The components thus obtained were mixed in the following quantities: about 0.01% by weight *Lactobacillus brevis* HY7401, about 0.01% by weight *Lactobacillus fermentum* CS332, about 0.01% by weight *Lactobacillus acidophilus* CSG, about 0.01% by weight *Bifidobacterium longum* HY8001, about 35% by weight Alder tree extract, about 40% by weight Selfheal extract, about 0.5% by weight milk thistle extract, about 2% by weight green bean-rice bran fermentation extract, about 0.16% by weight turnip extract, about 1% by weight tomato extract, about 0.3% by weight broccoli extract, about 0.2% by weight pineapple extract, about 3.5% by weight colostrum powder, about 4.8% by weight betaine, about 2.5% by weight composite vitamin premix, and about 10% by weight water, on the basis of the total weight of the composition for use in liver function improvement, blood alcohol level reduction and in-vivo antioxidant activity enhancement.

In combination with usual carriers or expedients, the composition may be used to prepare various functional beverages, fermented foods, health foods, etc.

EXAMPLE 2

Preparation of Fermented Dairy Food Based on the Composition for Liver Function Improvement, Blood Alcohol Level Reduction and In-Vivo Antioxidant Activity Enhancement A fermented dairy food comprising the composition for liver function improvement, blood alcohol level reduction and in-vivo antioxidant activity enhancement and a mixed fruit syrup was prepared as follows.

First, a lactic acid culture was prepared. In this regard, about 95.36% by weight of raw milk was mixed with about 4.6% by weight of skim milk powder (or mixed dried milk) with stirring to give a mixture which ranged in density at 15° C. from about 1.0473 to about 1.0475, in titrable acidity from about 0.200 to 0.220%, in pH from about 6.65 to about 6.70, and in Brix° at 20° C. from about 16.3 to about 16.5%. Subsequently, the mixture was subjected to UHT treatment (for 2 sec at 135° C.) and cooled to 40° C., followed by inoculation with *Streptococcus thermophilus* and lactase (Valley laboratory, USA) in an amount of about 0.02% by weight each. Cultivation for 6 hours afforded the lactic acid culture which contained bacteria at a total density of $1.0 \times 10^9$ cfu/ml or more on a BCP medium and ranged in titrable acidity from about 0.89 to about 0.91% and in pH from about 4.55 to about 4.65.

The mixed fruit syrup was prepared by mixing about 10~15% by weight of high fructose corn syrup, about 3~5% by weight of white sugar, about 3~5% by weight of brown sugar, about 10~15% by weight of a mixed juice concentrate having 56 Brix°, about 0.1~1.0% by weight of pectin, about 0.05~0.15% by weight of a fresh fruit mix essence and about 58.85~73.85% by weight of water at about 30~35° C. with stirring, conducting UHT treatment (135° C., 2 sec) for sterilization, and cooling the mixture.

about 35~50% by weight of the lactic acid bacteria culture, about 5.5~7.0% by weight of the composition for liver function improvement, blood alcohol level reduction and in-vivo antioxidant activity enhancement, and about 43.0~59.5% by weight of the mixed fruit syrup were mixed to homogeneity at 150 bar and cooled to 10° C. or lower to obtain a fermented milk food useful for liver function improvement, blood alcohol level reduction and in-vivo antioxidant activity enhancement.

EXAMPLE 3

Preparation of Functional Beverage Based on the Composition for Liver Function Improvement, Blood Alcohol Level Reduction and In-Vivo Antioxidant Activity Enhancement A functional beverage composed of the composition for liver function improvement, blood alcohol level reduction and in-vivo antioxidant activity enhancement and a mixed fruit syrup was prepared as follows.

The mixed fruit syrup was obtained by mixing about 10~15% by weight of high fructose corn syrup, about 3~5% by weight of white sugar, about 3~5% by weight of brown sugar, about 10~15% by weight of a mixed juice extract having 56 Brix° out 0.1~1.0% by weight of pectin, about 0.05~0.15% by weight of a fresh fruit mix essence and about 58.85~73.85% by weight of purified water at about 30~35° C. with stirring, conducting UHT treatment (135° C., 2 sec) for sterilization, and cooling the mixture.

about 43.0~59.5% by weight of this mixed fruit syrup, about 5.5~7.0% by weight of the composition useful for liver function improvement, blood alcohol level reduction and in-vivo antioxidant activity enhancement, and about 33.5~51.5% by weight of purified water were mixed to homogeneity at 150 bar and cooled to 10° C. or lower. The solution thus obtained was packed in a container such as a glass bottle, a PET bottle, etc.

EXAMPLE 4

Preparation of Health Food Based on the Composition for Liver Function Improvement, Blood Alcohol Level Reduction and In-Vivo Antioxidant Activity Enhancement The composition useful for improving liver function, reducing blood alcohol levels and enhancing in-vivo antioxidant activity in accordance with the present invention can be formulated alone or in combination with pharmaceutically acceptable expedients or carriers into tablets, capsules, etc.

On the basis of the composition, a health food for use in liver function improvement, blood alcohol level reduction and in-vivo antioxidant activity enhancement was prepared as follows.

After being pasteurized at 65° C. for 15 min and cooled, the composition for liver function improvement, blood alcohol level reduction and in-vivo antioxidant activity enhancement was subdivided into a predetermined amount and immediately lyophilized and pulverized. The powder was sealed for commercial use.

TEST EXAMPLE 1

Reduction of Blood Alcohol Content

For use in experiments, 5-week-old Sprague-Dawley (SD) lineage male rats (Daehan Biolink Co., Ltd.) were pre-reared at a temperature of 25±1° C. and at a relative humidity of 50±5% with solid foodstuff (CJ Co.,) for one week.

Upon the administration of the composition useful for the improvement of liver functions, the reduction of blood alcohol levels and the enhancement of in-vivo antioxidant activity, the blood alcohol level-reducing effect was examined in the following animal tests.

The compound of the present invention useful for liver function improvement, blood alcohol level reduction and in-vivo antioxidant activity enhancement was administered at a dose of 5 ml/kg B.W. for two weeks while phosphate buffered saline (PBS) was orally administered as a control at a dose of 5 ml/kg B.W. for two weeks by compulsion. The test group and the control group each consisted of 5 rats. On the 15$^{th}$ day of the test, the compound of the present invention and PBS were administered to the test group and the control group, respectively, at a dose of 5 ml/kg B.W. every 30 min after the administration, a 22% alcohol solution was orally administered at a dose of 4 g/kg B.W. to both the test group and the control group by compulsion. A predetermined time period after the alcohol administration, 100 μl of blood was sampled from the lateral tail vein of each rat using heparinized capillary tubes. 1 ml of dichloromethane was added to each of the blood samples which was then vigorously vortexed. After treatment with a small amount of anhydrous sodium sulfate ($Na_2SO_4$) to remove moisture and filtration, the blood samples were analyzed for alcohol level in blood. Blood sampling after alcohol administration was conduced at regular intervals. The alcohol content of the blood were determined using a gas chromatography system (Hewlett Packard HP6890, GC) equipped with a flame ionization detector (FID), with blood samples injected with the aid of an autosampler (HP G1512A). The mobile phase was nitrogen gas. The GC column was a DB-Wax column (30 m×0.25 mm×0.15 μm; Agilent). The quantitative analysis was performed under the condition that the injector was maintained at 200° C. and the column was temperature programmed from 55 to 70° C. at 10° C./min, and maintained for 2 min at 55° C. and for 4 min at 70° C. Ethyl acetate was used as an internal standard material.

As depicted in FIG. 1, the results of analysis demonstrate that the composition for liver function improvement, blood alcohol level reduction and in-vivo antioxidant activity enhancement in accordance with the present invention has superior capacity to reduce blood alcohol levels as compared to the control.

TEST EXAMPLE 2

Hepatoprotective Activity of the Composition for Counteracting Chronic Alcohol Drinking Experimental animals, previously reared for one week, were divided into a control group, an alcohol group, and a composition group, each consisting of 6 rats. Compulsory oral administration was conducted for 2 weeks with PBS (5 ml/kg B.W.) on both the control group and the alcohol group and with the composition for liver function improvement, blood alcohol level reduction and antioxidant activity enhancement (5 ml/kg B.W.) in accordance with the present invention on the composition group, with the concomitant administration of a 22% alcohol solution (3 g/kg B.W.) to both the alcohol group and the composition group for the same period. After the final administration on the 14$^{th}$ day of the test, all of the rats were starved for 24 hours. Then, the animals were anesthetized in an ether atmosphere and a ventral midline incision was made in the abdomen. Blood was sampled from the abdominal aorta and bleeding was allowed to continue until death. Using a hematology analyzer (Prime, BioSED), the blood samples were measured for AST (Aspartate aminotransferase) and ALT (Alanine aminotransferase) levels. These levels are shown in FIGS. 2a and 2b, respectively.

Figure 2A:
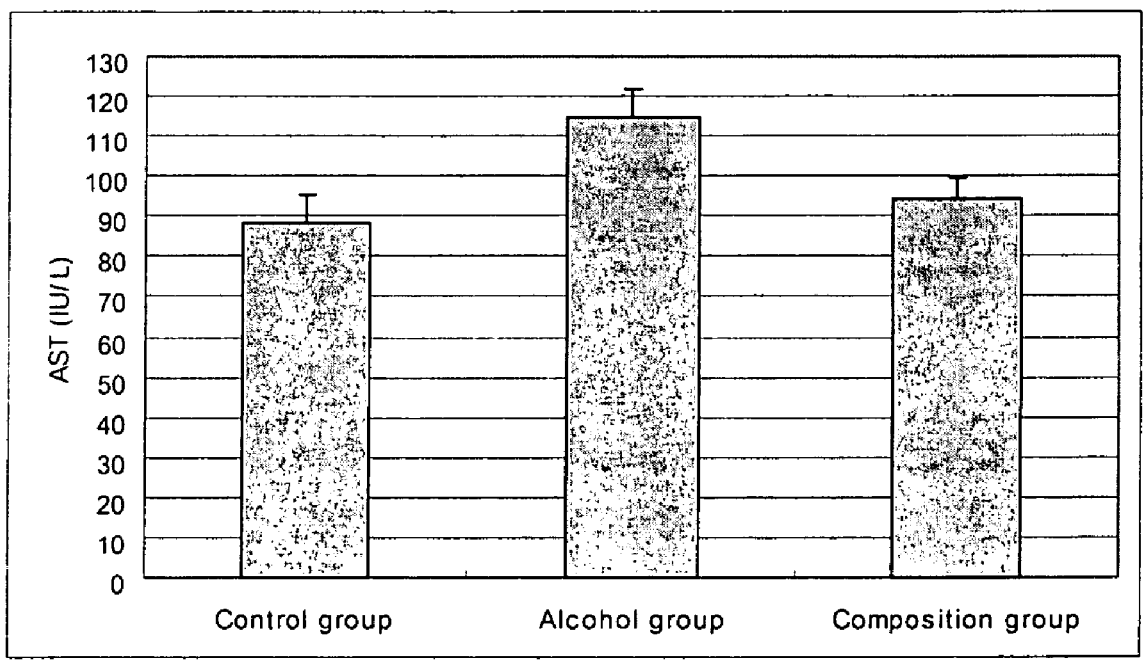
FIG. 2*a* is a graph showing the ability of the composition of the present invention to decrease AST levels to counteract chronic alcohol drinking in animal tests.
Figure 2B:
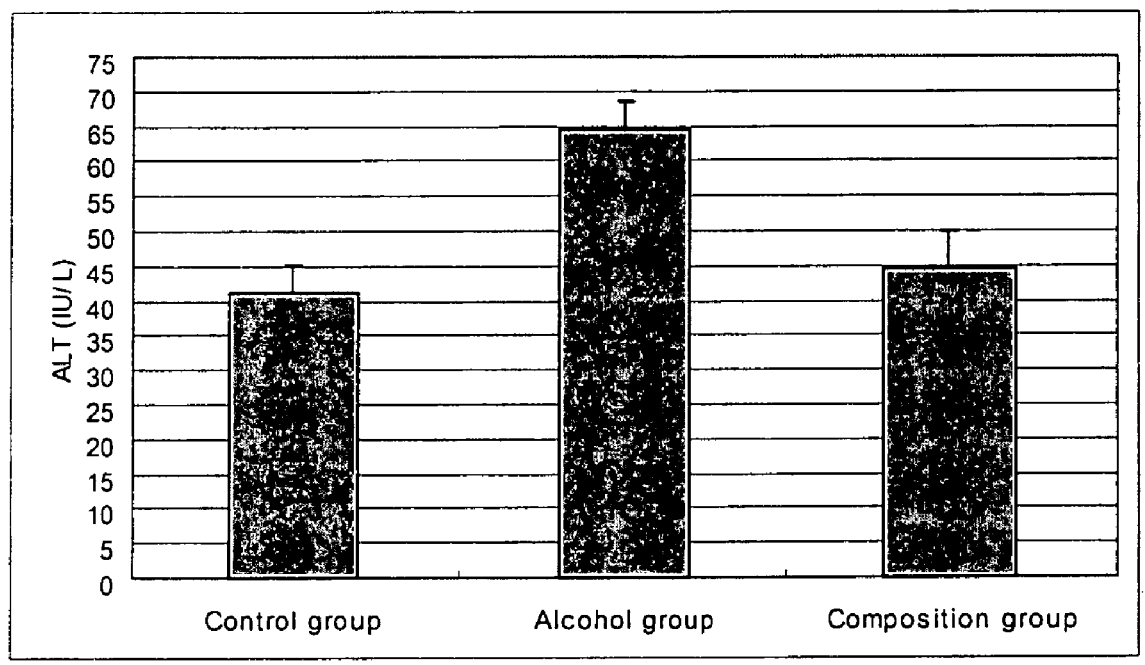
FIG. 2*b* is a graph showing the ability of the composition of the present invention to decrease ALT levels to counteract chronic alcohol drinking in animal tests.

As is apparent from the graphs of FIGS. 2a and 2b, the group to which the composition for liver function improvement, blood alcohol level reduction and in-vivo antioxidant activity enhancement was administered had significantly reduced AST and ALT levels compared to the alcohol group, demonstrating the hepatoprotective activity of the composition against alcohol.

TEST EXAMPLE 3

Antioxidant Effect of the Composition Assay for Antioxidant Activity Enhancement by Increase in Hepatic GSH S-Transferase Activity and Decrease in SOD Activity In a manner similar to that of Test Example 2, the materials were compulsorily administered to rats which were then bled to death. The livers of the blood-depleted rats were perfused with 4° C. physiological saline to remove remaining blood, and excised there from. A predetermined sized piece of the liver was put in four volumes of a 0.25M sucrose solution (with a content of 0.5 mM EDTA) and homogenized in an ice bath using a glass and teflon homogenizer. The homogenized solution was centrifuged at 600×g for 10 min to remove nuclei and uncrushed organelles and then at 10,000×g for 20 min to remove mitochondrial fractions. Subsequently, ultra-centrifugation at 105,000×g for one hour resulted in a cytosolic fraction as a supernatant. This cytosolic fraction was used for the measurement of glutathione S-transferase (GSH S-transferase) and superoxide dismutase activity. To assay the enzymatic activity, the protein content of the cytosolic fraction was measured using a protein assay kit (Bio-rad).

GSH S-transferase activity was assayed as follows. In a mixture of 10 μl of the cytosolic fraction, 2.935 ml of 0.1M PBS (pH 6.5), 25 μl of 0.12M 2-4CNDB (1-chloro-2,4-dinitrobenzene), and 30 μl of 0.1M reductive glutathione, a 3 min reaction at 25$^2$C was monitored at intervals of 20 sec at 340 nm. The enzyme activity was defined as the amount of 2,4-dinitrobenzene-glutathione produced in one min per mg of enzyme protein using the molecular absorbance coefficient of 2,4-dinitrobenzene-glutathione (E mM/340 nm=9.6 mM$^{-1}$ cm$^{-1}$) [Habig et al. J. Biol. Chem. 249:7130-7139 (1985)]. The GSH S-transferase activity was compared between the control group and the composition group to obtain % enzyme activity increase, the results of which are given in FIG. 3a.

Figure 3A:
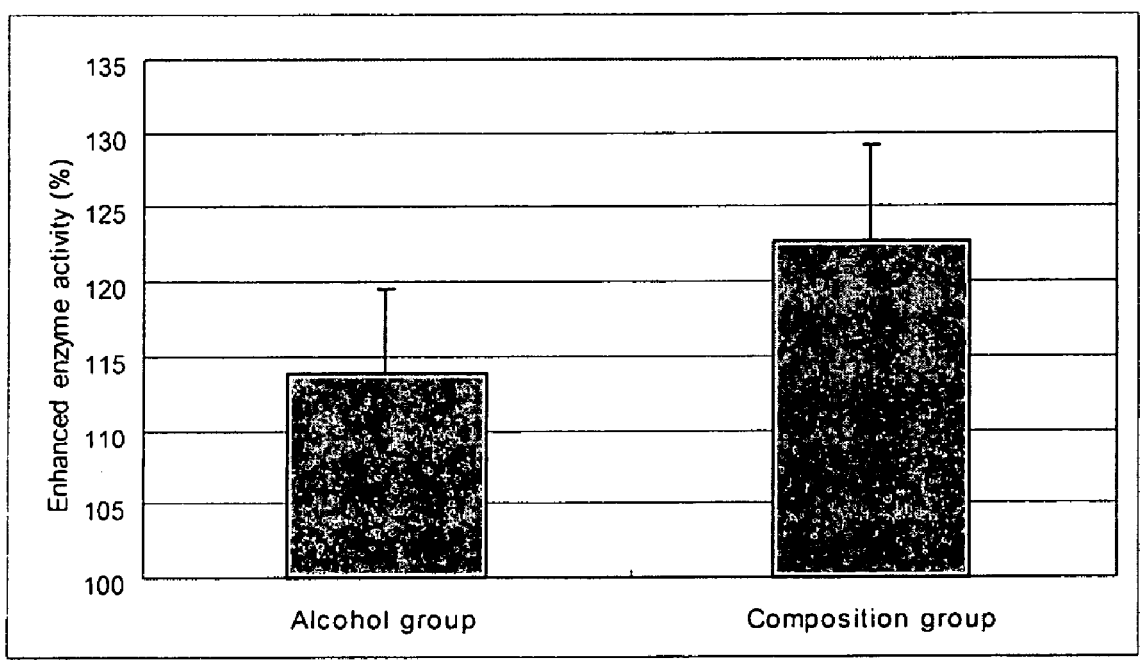
FIG. 3*a* is a graph showing the ability of the composition of the present invention to activate GSH S-transferase to counteract chronic alcohol drinking in animal tests.

As shown in FIG. 3a, GSH S-transferase activity correlating with the detoxification of the liver increased upon alcohol administration to 113% in the alcohol group and to 122% in the composition group. Thus, the administration of the composition further enhances the hepatic enzyme activity responsible for antioxidation.

SOD activity was assayed as follows. A mixture of 2.8 ml of a 50 mM Tris HCl buffer (10 mM EDTA, pH 8.6) and 0.1 ml of 15 mM pyrogallol was pre-incubated at 5° C. for 5 min, followed by the addition of 0.1 ml of the cytosolic fraction thereto. The resulting 3.0 ml solution was allowed to react at 25° C. for 10 min, and the reaction was stopped with 0.1 ml of 1N HCl. Changes in absorbance at 440 nm were measured. The amount of SOD (U/mg of protein) necessary for 50% inhibition of the autooxidation of the 15 mM pyrogallol solution reacting in the absence of the SOD was defined as one unit of enzyme activity [Marklund and Marklund. Eur. J. Biochem. 47:469-474 (1974)]. The enzyme activity in the control group, the alcohol group and the composition group were measured and compared there among as shown in FIG. 3b.

Figure 3B:
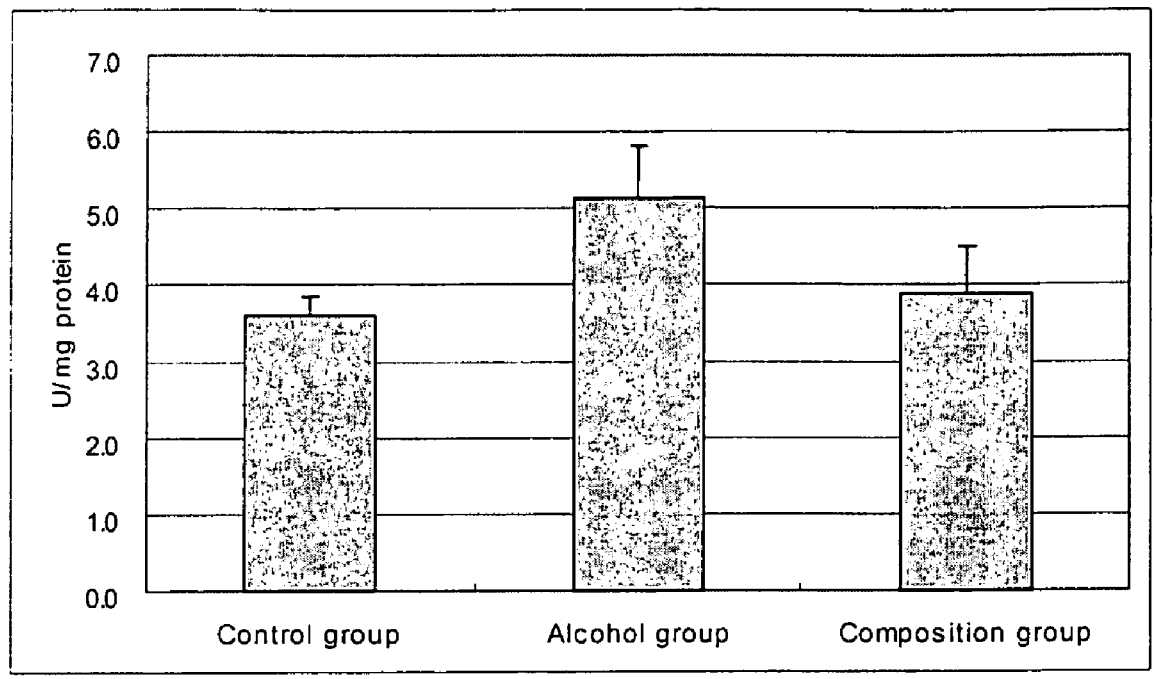
FIG. 3*b* is a graph showing the ability of the composition of the present invention to enhance antioxidant activity by deactivating SOD to counteract chronic alcohol drinking in animal tests.

As apparent from the data of FIG. 3b, the enzyme activity of the composition group (3.9 U/mg) is comparable with that of the control group (3.6 U/mg), but much lower than that of the alcohol group (5.2 U/mg), demonstrating that the composition enhances hepatic antioxidant activity to reduce the level of superoxide in hepatocytes.

Assay for Reduction of Lipid Peroxidation in Hepatocytes

To 0.1 ml of a liver homogenate, 0.2 ml of 8.1% sodium dodecyl sulfate (SDS), 1.5 ml of 20% acetic acid buffer (pH 3.5), and 1.5 ml of 0.8% thiobarbituric acid were added, and distilled water was added to a total amount of 4 ml. This resulting solution was allowed to react at 95° C. for one hour. After completion of the reaction, the solution was cooled to room temperature and mixed with 1 ml of distilled water and 5 ml of a mixture of butanol:pyridine (15:1). After centrifugation at 4,000 rpm for 10 min, the supernatant was measured for absorbance at 532 nm. A standard curve was established with the standard material 1,1,3,3-tetraethoxypropane. From the standard curve, concentrations of malone dialdehyde (MDA) were calculated in nmoles MDA/g of liver [Okawa et al., Anal. Biochemistry 95:35-41 (1979)]. MDA concentrations (nmoles/g) of the control group, the alcohol group and the composition group are shown in FIG. 3c.

Figure 3C:
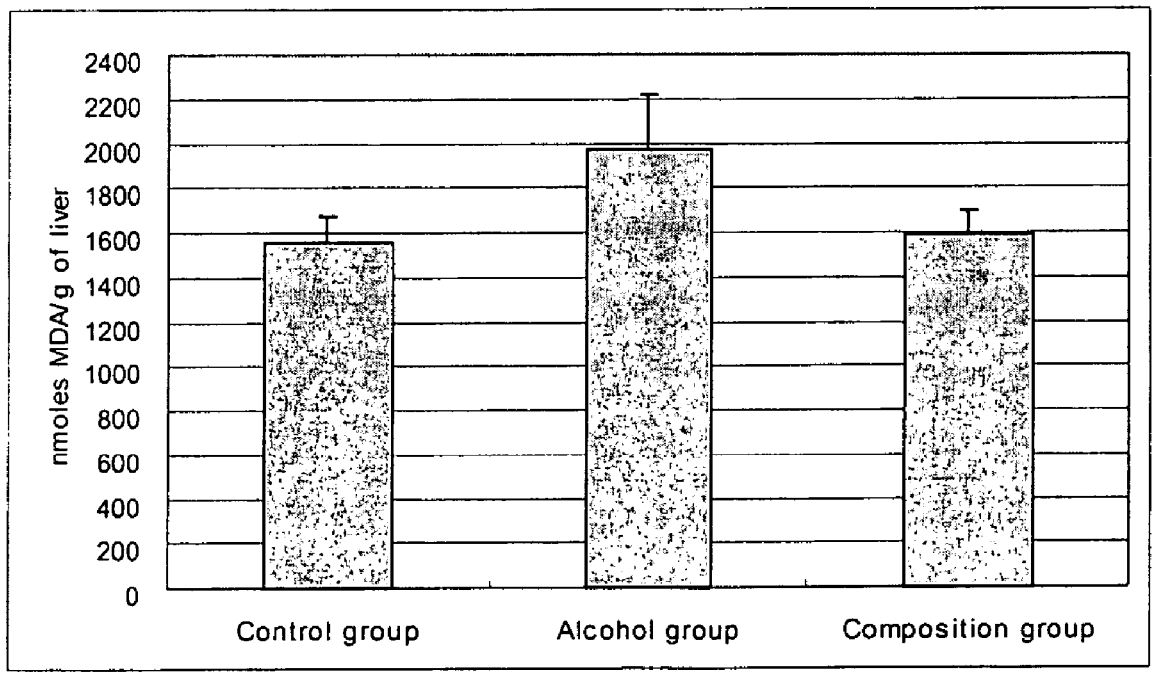
FIG. 3*c* is a graph showing the ability of the composition of the present invention to prevent lipid peroxidation within hepatocytes to counteract chronic alcohol drinking in animal tests.

As seen in FIG. 3c, the MDA concentration (nmoles/g) of the composition group is lower than that of the alcohol group, demonstrating that hepatic lipid peroxidation was better inhibited in the composition group than in the alcohol group.

TEST EXAMPLE 4

Alcohol Metabolism Stimulation of the Composition in the Human Body

The cytosolic fraction of rat livers prepared in Test Example 3 was examined for alcohol dehydrogenase activity. To a solution of 2.5 mM of nicotineamide adenine dinucleotide ($NAD^+$) in 0.1M glycine buffer (pH 9.6), ethanol was added to form a final concentration of 25 mM. 100 μl of the cytosolic fraction was added to the solution so as to initiate a reaction in a 25° C. incubation bath. After completion of the reaction, reductive nicotineamide adenine dinucleotide (NADH) was quantitatively analyzed by measuring absorbance at 340 nm and 25° C. using a spectrophotometer. Alcohol dehydrogenase activity was calculated in protein (mg) of the cytosolic fraction and in the amount of the reductive nicotineamide adenine dinucleotide (NADH) produced per time [Nosova et al., Alcohol & Alcoholism. 35:561-568 (2000)]. Alcohol dehydrogenase activities of the control group, the alcohol group and the composition group are shown in graph form in FIG. 4.

Figure 4:
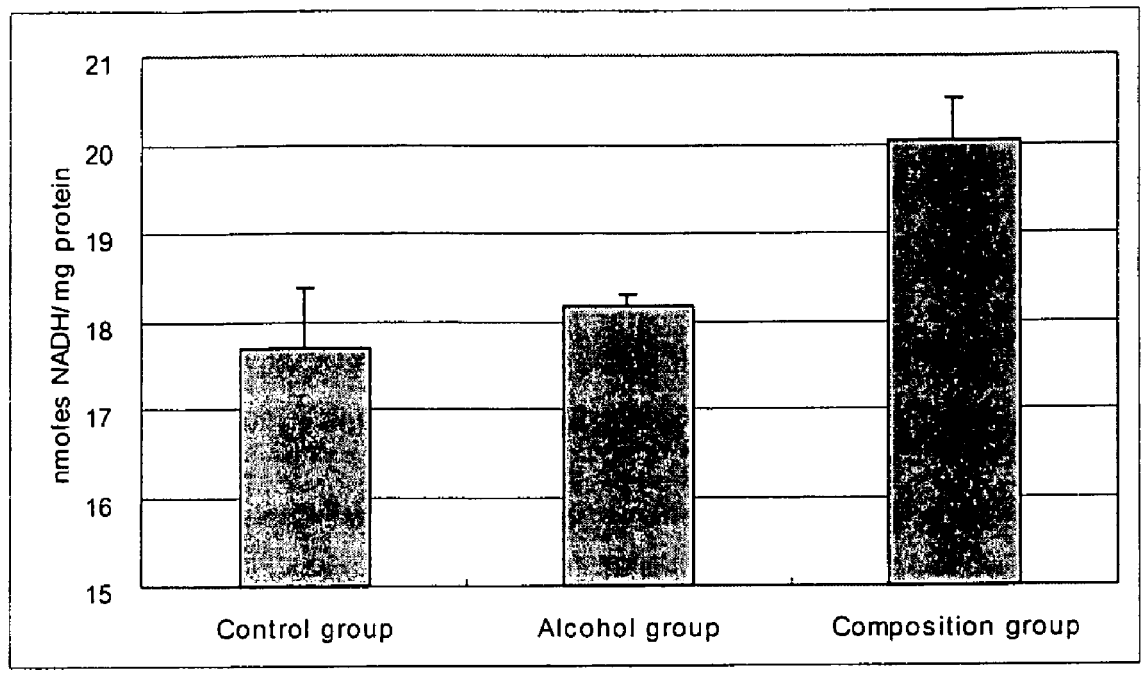
FIG. 4 is a graph showing the ability of the composition of the present invention to increase alcohol dehydrogenase activity in animal tests.

As shown in FIG. 4, the composition group increased in alcohol dehydrogenase activity much more than did the alcohol group, indicating that the composition stimulates hepatic alcohol metabolism.

TEST EXAMPLE 5

Human Liver Function Improvement of the Composition

Of 18~60 years old volunteers for bodily function testing, the subjects of the test were selected if they were determined to be suitable by physicians and accepted the test purpose.

From among primary subjects who had AST of 50(IU/L) or higher, ALT 45(IU/L) or higher or γ-GTP 80(IU/L) or higher, with or without hepatitis B or C virus, 60 subjects for the assay for liver function improvement were finally selected after medical examination through interviews and detailed liver function testing.

Assays for liver function improvement were conducted as follows.

60 subjects for assays for liver function improvement were randomly divided into a placebo group, a positive control group and a composition group. Everyone in the placebo group, the positive control group and the composition group took respective test materials (150 ml) twice per day for 8 weeks. Liver function improvement was determined by comparing liver function indicators measured upon the selection of the final subjects (week zero) with those measured from the blood of persons who briefly fasted after 4 and 8 weeks of sample administration. Serum separated from 3 ml of whole blood by centrifugation at 2,500 rpm for 10 min was measured for liver test indicators including AST (Aspartate aminotransferase), ALT (Alanine aminotransferase), and γ-GTP (γ-glutamyl transpeptidase), using a biochemical automatic analyzer (Hitachi 7600-110, 7170 automatic analyzer).

In order to perfectly conduct the test, the test materials used in Test Example 5 were packed in completely identical containers and kept cold while being transported to the research lab. Under the management of a research supervisor, the test materials in cold storage were supplied directly to the subjects of respective test groups. The test materials had the same appearance, so that the subjects could not distinguish them. The placebo was prepared by sterilizing a solution of the same mixed juice extract and high fructose corn syrup in water at 135° C. for 2 sec so as to provide the same taste as the composition. As for the positive control (a liver function improver), it was prepared by mixing a bottle of the placebo with 18.9 ml of a *Carduus marinus* ext. suspension (*Carduus marinus* ext. 1.38 g in 100 ml of suspension).

Data obtained in this experiment was statistically processed using an SPSS/WIN 12.0 program. Using an independent samples t-test, the mean scores on a dependent variable for two independent groups were compared. A paired samples T test compares the means of two variables. It computes the difference between the two variables for each case. The One-way ANOVA was used to test the equality of three or more means at one time by using variances. The Bonferroni correction was responsible for the post-statistic analysis. For repeatedly measured data, a repeated measures ANOVA was used, with the post-analysis for differences between groups corrected with the Bonferroni method.

Figure 5A:
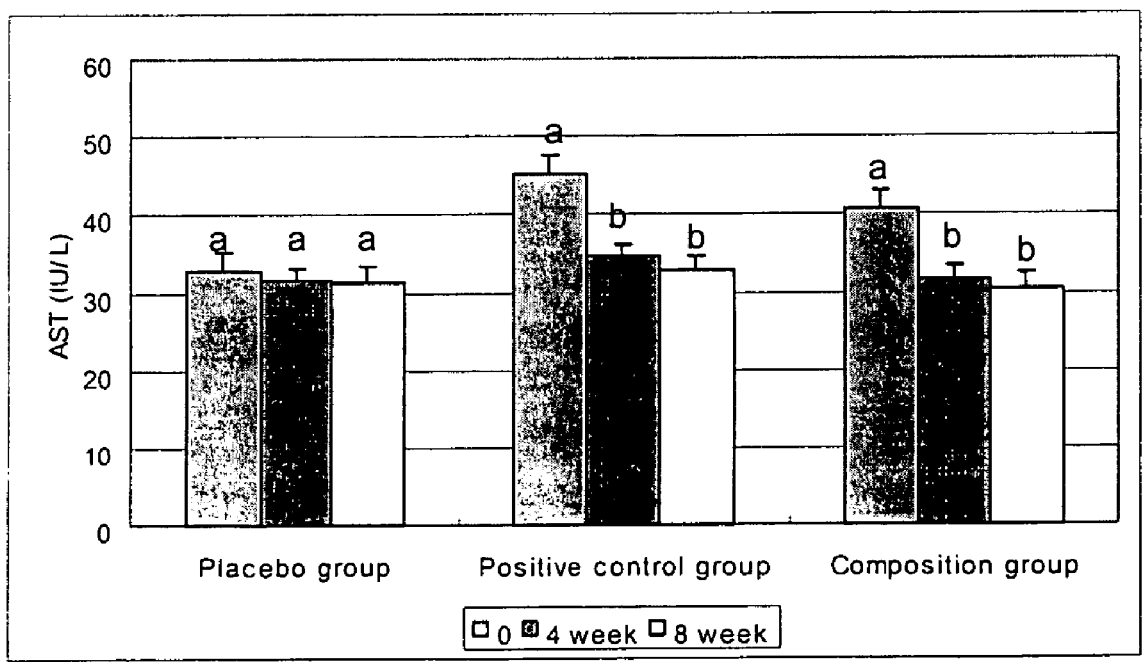
FIG. 5a is a graph showing the ability of the composition of the present invention to reduce AST levels in the human body.

Statistical analysis data for the effects of the composition of the present invention on human liver functions are shown in graph form in FIGS. 5a [a, b: there are significant differences between different letters in each group ($p<0.05$)], 5b [a, b, c: there are significant differences between different letters in each group ($p<0.05$)], and 5c [a, b: there are significant differences between different letters in each group ($p<0.05$)].

Figure 5B:
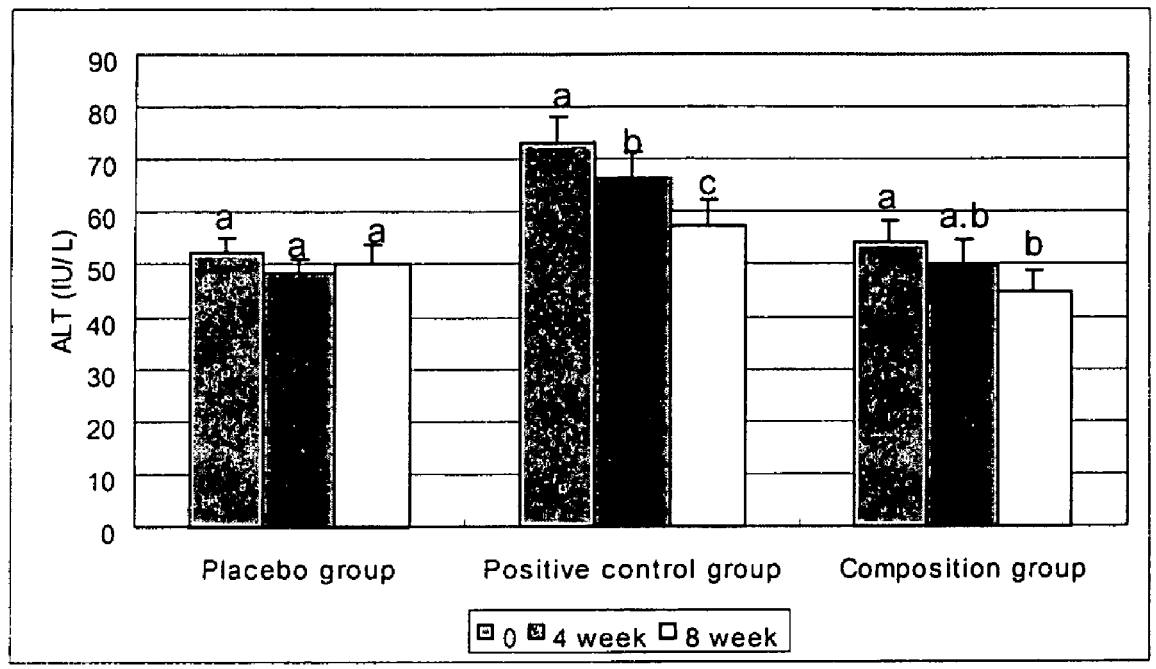
FIG. 5b is a graph showing the ability of the composition of the present invention to reduce ALT levels in the human body.
Figure 5C:
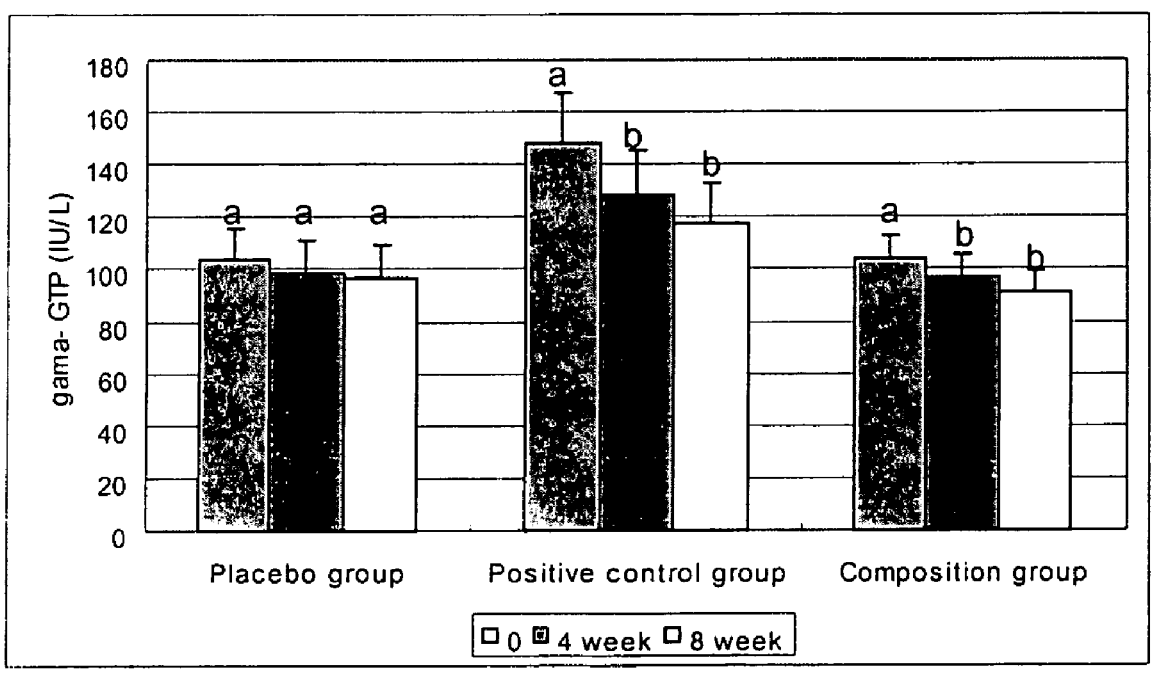
FIG. 5c is a graph showing the ability of the composition of the present invention to reduce γ-GTP levels in the human body.

As is apparent from data of FIGS. 5a, 5b, and 5c, the composition group decreased in the levels of the liver function indicators (AST, ALT, γ-GTP). Particularly, the AST level in the composition group was decreased to about 80% of that attributed to the commercially available liver medication (AST levels at week zero to 8).

TEST EXAMPLE 6

Blood Alcohol Level Reduction of the Composition in the Human Body

The subjects for assay for alcohol metabolism capacity were persons who had not suffered genetic or chronic diseases and were medicinally determined to have no symptoms of internal disease or symptoms and to be suitable for the assay on the basis of the results of clinical assays such as serological tests, serochemical tests, urine tests, etc. The assay for in-vivo alcohol metabolism was conducted in a cross-over trial manner in which 26 subjects were randomly divided into two group: a placebo-composition group, in which 13 subjects were treated first with placebo for 2 weeks and then with the composition for liver function improvement, blood alcohol level reduction and in-vivo antioxidant activity enhancement, with a 3-week intermission between the treatments; and a composition-placebo group, in which 13 subjects were treated first with the composition for 2 weeks and then with the placebo for 2 weeks, with a 3-week intermission between the treatments.

Both the placebo-composition group and the composition-placebo group took the test materials (150 ml) twice a day (morning and evening) for 2 weeks. Blood sampling was conducted on subjects who had temporarily fasted just before the intake of the test samples and just after completion of the intake of the test samples for two weeks so as to analyze levels of alcohol in the blood and compare alcohol metabolism capacities. After the primary testing, the subjects were stabilized during the three week intermission. In the same manner but reciprocally, secondary testing was conducted. In order to compare the effects of the composition on alcohol metabolism in the course of the two rounds of testing, all the subjects took the same alcoholic beverage (50 ml, 40% vol) within 1 min on the last day of each of the primary and the secondary testing. To examine the change in blood alcohol levels of individuals, blood samples were taken 8 times during a predetermined period of time from just before the alcohol intake to 4 hours after the alcohol intake (0 min, 20 min, 40 min, 60 min, 90 min, 120 min, 180 min, and 240 min). Blood alcohol levels were measured using a calorimetric method. For convenience, blood was sampled with the aid of a heparinized angio-catheter.

Blood alcohol levels were analyzed as follows. The measurement and computation of blood alcohol levels was conducted with the COBAS INTEGRA system (Integra 400, Roche, Germany). A suspension of 2 µl of sampled serum in an R1 buffer (buffer reagent: 300 mmol/L 1,3-diamino-2-hydroxypropane buffer, pH 9.0) was mixed with 40 µl of an R2 buffer (enzyme reagent: 50 mmol/L sodium citrate, 36 mmol/L NAD, and $\geq$2000µ kat/L alcohol dehydrogenase) and then with distilled water to a final volume of 245 µl. Absorbance at 378/409 nm was measured to calculate blood alcohol concentrations (%).

Figure 6A:
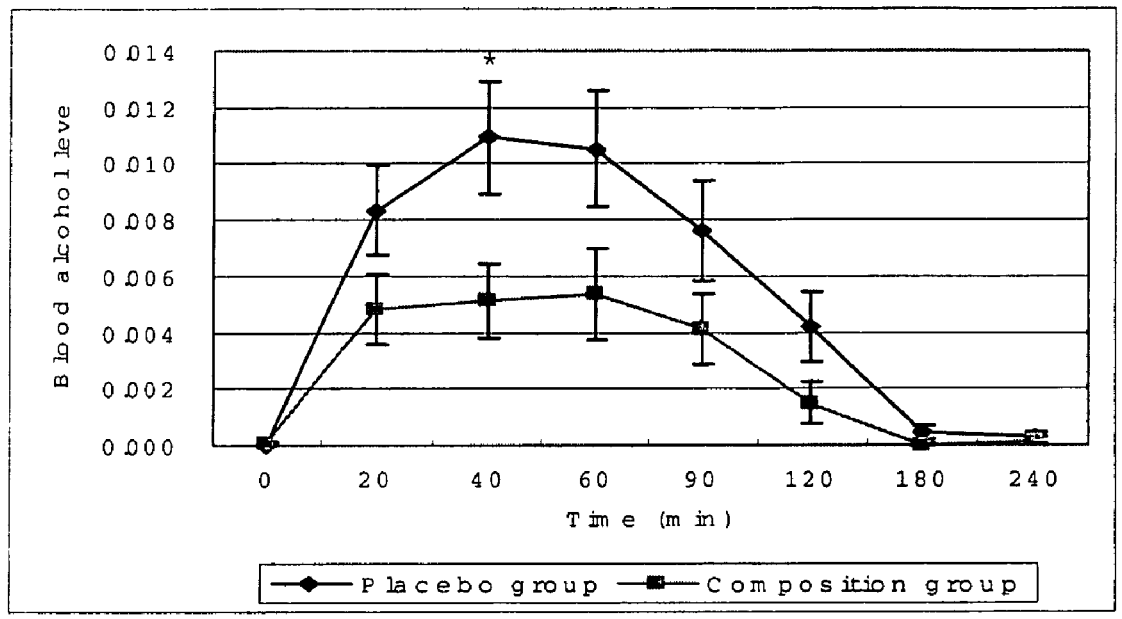
FIG. 6a is a graph showing the ability of the composition of the present invention to reduce blood alcohol levels in the human body (primary testing)

Data of the blood alcohol concentrations were statistically processed using an SPSS/WIN 12.0 program and the results are plotted in FIGS. 6a (*: $p<0.05$. paired t-test for difference within groups) and 6b (*: $p<0.05$. paired t-test for difference within groups).

Figure 6B:
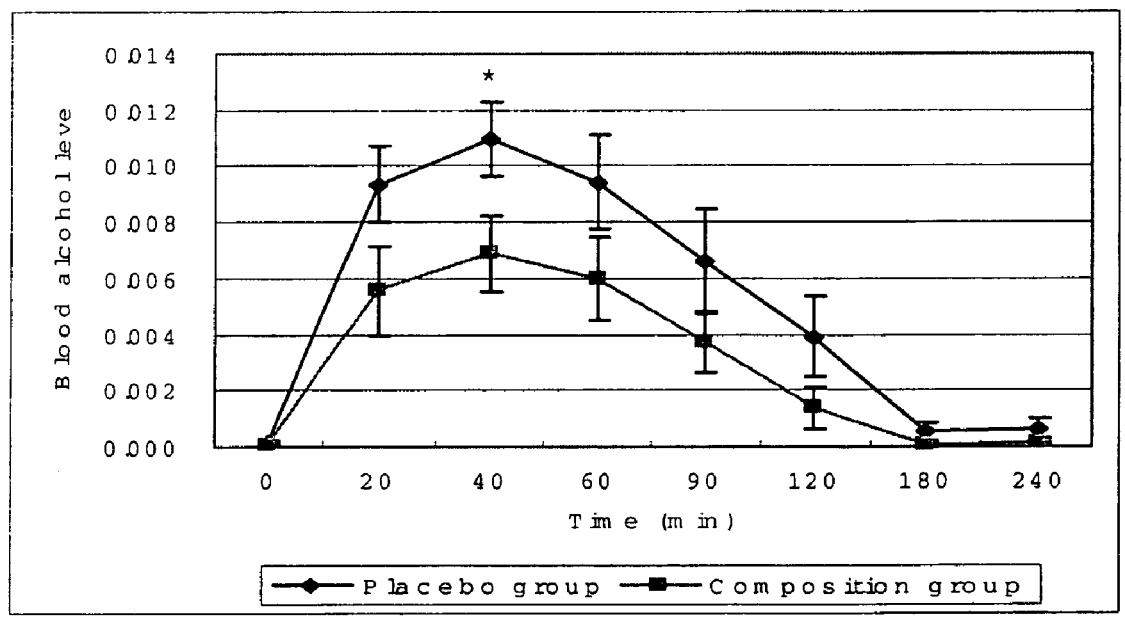
FIG. 6b is a graph showing the ability of the composition of the present invention to reduce blood alcohol levels in the human body (secondary testing)

As seen in FIGS. 6a and 6b, the blood alcohol level of the composition of the present invention was greatly decreased compared to that of the control group for both primary and secondary testing.

TEST EXAMPLE 7

Antioxidant Activity Enhancement of the Composition in the Human Body

The assay for in-vivo antioxidant activity of the composition was conducted on the same subjects who were used in the assay for alcohol metabolism enhancement of Test Example 6. Both the placebo-composition group and the composition-placebo group took the test materials (150 ml) twice a day (morning and evening) for 2 weeks. Blood was sampled from the subjects, who had temporarily fasted, just before the intake of the test samples and just after completion of the intake of the test samples for two weeks so as to detect the difference in the antioxidant activity effect therebetween through the analysis of TAS (total antioxidant status) and TBARS (thiobarbituric acid reactive substance). After the primary testing, the subjects were stabilized during the three week intermission. In the same manner but reciprocally, secondary testing was conducted.

TAS assay was performed with a total antioxidant status assay kit (Randox Lab. Ltd., UK) based on the measurement of the absorbance of ABTS free radical cations formed by the interaction of ABTS [2,2'-Azino-di-(3-ethylbenzthiazoline sulphonate)] with ferry myoglobin radical species, produced by activating a peroxidase (metmyoglobin) with hydrogen peroxide. A suspension of 2 µl of sampled serum in 1 ml of chromogen was allowed to react at room temperature for 1 min, followed by measuring the absorbance at 600 nm thereof ($A_1$). To this was added 200 µl of a substrate and 3 min later, absorbance was measured again at the same wavelength ($A_2$). TAS concentrations (mmol/L) were calculated according to the following equation.

$A_2 - A_1 = \Delta A$ of sample/standard/blank

Total Antioxidant Status;

Factor=conc. of standard/($\Delta$ A blank−$\Delta$ A standard) mmol/L Therefore, TAS concentration=Factor×($\Delta$ A Blank−$\Delta$ A Sample)

The inhibitory activity against lipid peroxidation was assayed using a kit (CALBIOCHEM, CA, USA) with 1,1,3,3-tetramethoxypropane (TMOP) used as a standard material. 200 µl of the plasma separated from whole blood from the subjects was suspended in 650 µl of R1 (N-methyl-2-phenylindole in acetonitrile), agitated for 3-4 sec and mixed with 150 µl of R2 (methanesulfonic acid) buffer. This suspension was allowed to react at 45° C. for 60 min before the measurement of absorbance at 586 nm. OD values measured were applied to a standard curve to calculate MDA levels.

Figure 7A:
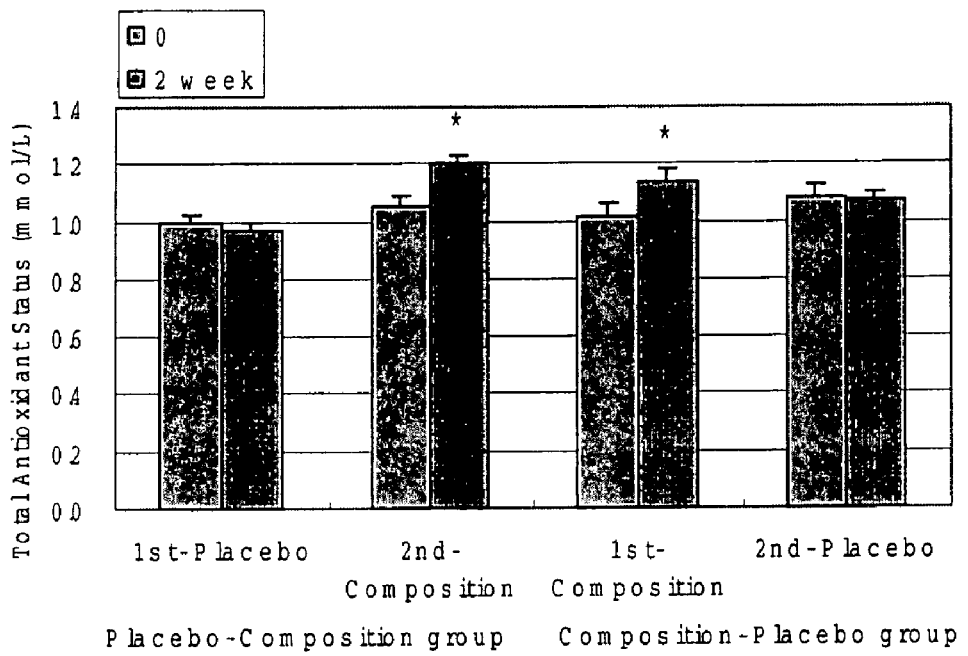
FIG. 7a is a graph showing the ability of the composition of the present invention to enhance TAS (total antioxidant status) in the human body.

Data of the assay for in-vivo antioxidant activity and inhibitory activity against lipid peroxidation was processed using an SPSS/WIN 12.0 program in the same manner as in Test Example 5, and the statistic results are visualized in FIGS. 7a (*: $p<0.05$, paired t-test for differences within groups) and 7b (*: $p<0.05$, paired t-test for differences within groups).

Figure 7B:
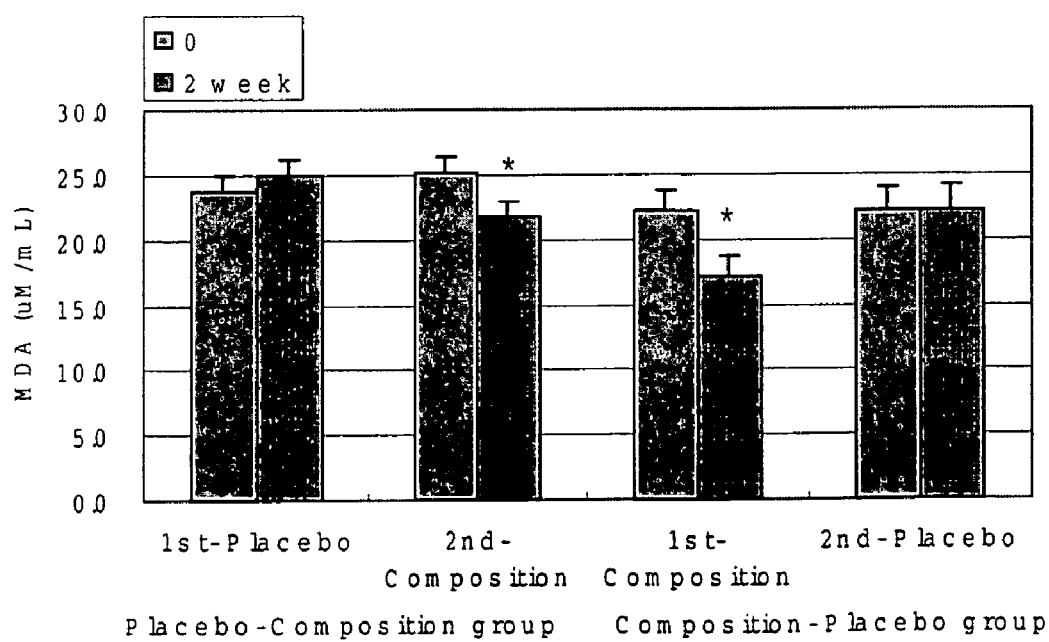
FIG. 7b is a graph showing the ability of the composition of the present invention to decrease TBARS (thiobarbituric acid reactive substance) levels in the human body.

As shown in FIGS. 7a and 7b, the intake of the composition for liver function improvement, blood alcohol level reduction and in-vivo antioxidant activity enhancement according to the present invention was found to increase TAS and reduce TBARS in both primary and secondary testing.

As described hereinbefore, a composition comprising Lactobacillus brevis HY7401, Lactobacillus fermentum CS332, Lactobacillus acidophilus CSG, Bifidobacterium longum HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamin $B_1$, $B_2$, $B_3$, $B_6$, $B_9$, $B_{12}$ C, and E in accordance with the present invention can improve decreased liver function and shows excellent hepatoprotective and hepatocurative activity against alcohol upon excessive or habitual drinking with the ability to reduce blood alcohol levels. Its superior enhancement of in-vivo antioxidant activity also contributes to the use of the composition in the prevention of liver diseases and the improvement of liver function.

Examples are described in terms of the preferred embodiment of present invention. However, it should be understood that such disclosure is not limited to the explicit description of the present invention. The description and the claims of present invention are to be interpreted as covering all alterations and modifications within the true scope of this invention.

What is claimed is:

1. A composition for liver function improvement, blood alcohol level reduction and in-vivo antioxidant activity enhancement, comprising Lactobacillus brevis HY7401, Lactobacillus fermentum CS332, Lactobacillus acidophilus CSG, Bifidobacterium longum HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C and E.

2. The composition according to claim 1, wherein, the Lactobacillus brevis HY7401 is in a form of a freeze-dried powder at a density of $10^{11}$ cfu per g, the Lactobacillus fermentum CS332 is in a form of freeze-dried powder at a density of $10^{11}$ cfu per g, the Lactobacillus acidophilus CSG is in a form of a freeze-dried powder at a density of $10^{11}$ cfu per g, the Bifidobacterium longum HY8001 is in a form of a freeze-dried powder at a density of $10^{11}$ cfu per g, the Alder tree extract is an extract obtained by boiling xylem and bark of dried Alder tree in water for about 1 to about 5 hours, the Selfheal extract is an extract obtained by boiling dried Selfheal in water for about 1 to about 5 hours, the milk thistle extract has a total flavonoid content of 80% to 95% by weight and a sylibin content of about 28% to about 32% by weight, the green bean-rice bran fermentation extract is a commercially available green bean-rice bran fermentation extract in a liquid state, the turnip extract is in a liquid state with a Brix° of about 34 to about 36, the tomato extract is an extract prepared by grinding tomato fruits together with water, filtering the mixture, and spray-drying the filtrate, the broccoli extract is an extract prepared by grinding parboiled broccoli pieces, along with water, filtering the mixture, and spray-drying the filtrate, the pineapple extract is an extract prepared by grinding pineapple slices in water, filtering the mixture, and spray-drying the filtrate, the colostrum powder, when diluted 50,000-fold with distilled water, shows a titer of IgG specific for HAV (hepatitis A virus) in a range from about 1 to about 1.7 OD at 490 nm, the betaine is in an anhydrous form with a purity of about 99% to about 100% by weight, and the vitamins $B_1$, $B_2$, $B_3$, $B_6$, $B_9$, $B_{12}$, C, and E are in a composite premix form.

3. The composition according to claim 2, wherein, the *Lactobacillus brevis* HY7401 is contained in an amount from about 0.001% to about 0.1% by weight, the *Lactobacillus fermentum* CS332 in an amount from about 0.001% to about 0.1% by weight, the *Lactobacillus acidophilus* CSG in an amount from about 0.001% to about 0.1% by weight, the *Bifidobacterium longum* HY8001 in an amount from about 0.001% to about 0.1% by weight, the Alder tree extract in an amount from about 32% to about 36% by weight, the Selfheal extract in an amount from about 38% to about 42% by weight, the milk thistle extract in an amount from about 0.1% to about 0.8% by weight, the green bean-rice bran fermentation extract in an amount from about 1.0% to about 2.5% by weight, the turnip extract in an amount from about 0.1% to about 0.2% by weight, the tomato extract in an amount from about 0.8% to about 1.5% by weight, the broccoli extract in an amount from about 0.1% to about 0.5% by weight, the pineapple extract in an amount from about 0.15% to about 0.25% by weight, the colostrum powder in an amount from about 3.0% to about 4.0% by weight, the betaine in an amount from about 4.5% to about 5.0% by weight, and the composite vitamin premix in an amount from about 2.0% to about 3.0% by weight based on a total weight of the composition, and water is added in an amount from about 3.85% to about 18.24% by weight, based on the total weight of the composition.

4. A fermented dairy food, containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C, and E.

5. The fermented dairy food according to claim 4, wherein, the *Lactobacillus brevis* HY7401 is in a form of a freeze-dried powder at a density of $10^{11}$ cfu per g, the *Lactobacillus fermentum* CS332 is in a form of a freeze-dried powder at a density of $10^{11}$ cfu per g, the *Lactobacillus acidophilus* CSG is in a form of a freeze-dried powder at a density of $10^{11}$ cfu per g, the *Bifidobacterium longum* HY8001 is in a form of a freeze-dried powder at a density of $10^{11}$ cfu per g, the Alder tree extract is an extract obtained by boiling xylem and bark of dried Alder tree in water for about 1-5 hours, the Selfheal extract is an extract obtained by boiling dried Selfheal in water for about 1-5 hours, the milk thistle extract had a total flavonoid content of about 80% to about 95% by weight and a sylibin content of about 28% to about 32% by weight, the green bean-rice bran fermentation extract is a commercially available green bean-rice bran fermentation extract in a liquid state, the turnip extract is in a liquid state with a Brix° of 34 to 36, the tomato extract is an extract prepared by grinding tomato fruits together with water, filtering the mixture, and spray-drying the filtrate, the broccoli extract is an extract prepared by grinding parboiled broccoli pieces in water, filtering the mixture, and spray-drying the filtrate, the pineapple extract is an extract prepared by grinding pineapple slices in water, filtering the mixture, and spray-drying the filtrate, the colostrum powder, when diluted about 50,000-fold with distilled water, shows a titer of IgG specific for HAV (hepatitis A virus) in the range from about 1 to about 1.7 OD at 490 nm, the betaine is in an anhydrous form with a purity of about 99% to about 100% by weight, and the vitamins $B_1$, $B_2$, $B_3$, $B_6$, $B_9$, $B_{12}$, C, and E are in a composite premix form.

6. The fermented dairy food according to claim 5, wherein the *Lactobacillus brevis* HY7401 is contained in an amount from about 0.001% to about 0.1% by weight, the *Lactobacillus fermentum* CS332 in an amount from about 0.001% to about 0.1% by weight, the *Lactobacillus acidophilus* CSG in an amount from about 0.001% to about 0.1% by weight, the *Bifidobacterium longum* HY8001 in an amount from about 0.001% to about 0.1% by weight, the Alder tree extract in an amount from about 32% to about 36% by weight, the Selfheal extract in an amount from about 38% to about 42% by weight, the milk thistle extract in an amount from about 0.1% to about 0.8% by weight, the green bean-rice bran fermentation extract in an amount from about 1.0% to about 2.5% by weight, the turnip extract in an amount from about 0.1% to about 0.2% by weight, the tomato extract in an amount from about 0.8% to about 1.5% by weight, the broccoli extract in an amount from about 0.1% to about 0.5% by weight, the pineapple extract in an amount from about 0.15% to about 0.25% by weight, the colostrum powder in an amount from about 3.0% to about 4.0% by weight, the betaine in an amount from about 4.5% to about 5.0% by weight, and the composite vitamin premix in an amount from about 2.0% to about 3.0% by weight, based on a total weight of the composition, and water is added in an amount from about 3.85% to about 18.24% by weight based on the total weight of the composition.

7. A functional beverage, containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C, and E.

8. The functional beverage according to claim 7, wherein,
the *Lactobacillus brevis* HY7401 is in a form of a freeze-dried powder at a density of $10^{11}$ cfu per g,
the *Lactobacillus fermentum* CS332 is in a form of a freeze-dried at a density of $10^{11}$ cfu per g,
the *Lactobacillus acidophilus* CSG is in a form of a freeze-dried powder at a density of $10^{11}$ cfu per g,
the *Bifidobacterium longum* HY8001 is in a form of a freeze-dried powder at a density of $10^{11}$ cfu per g,
the Alder tree extract is an extract obtained by boiling the xylem and bark of the dried Alder tree in water for about 1-5 hours,
the Selfheal extract is an extract obtained by boiling dried Selfheal in water for 1-5 hours,
the milk thistle extract had a total flavonoid content of about 80% to about 95% by weight and a sylibin content of about 28% to about 32% by weight,
the green bean-rice bran fermentation extract is a commercially available green bean-rice bran fermentation extract in a liquid state,
the turnip extract is in a liquid state with a Brix° of 34 to 36,
the tomato extract is an extract prepared by grinding tomato fruits together with water, filtering the mixture, and spray-drying the filtrate,
the broccoli extract is an extract prepared by grinding parboiled broccoli pieces, along with water, filtering the mixture, and spray-drying the filtrate,
the pineapple extract is an extract prepared by grinding pineapple slices in the presence of water, filtering the mixture, and spray-drying the filtrate,
the colostrum powder, when diluted 50,000-fold with distilled water, shows a titer of the IgG specific for HAV (hepatitis A virus) in the range from about 1 to about 1.7 OD at 490 nm,
the betaine is in an anhydrous form with a purity of about 99% to about 100% by weight, and
the vitamins $B_1$, $B_2$, $B_3$, $B_6$, $B_9$, $B_{12}$, C, and E are in a composite premix form.

9. The functional beverage according to claim 8, wherein the *Lactobacillus brevis* HY7401 is contained in an amount from about 0.001% to about 0.1% by weight, the *Lactobacillus fermentum* CS332 in an amount from about 0.001% to about 0.1% by weight, the *Lactobacillus acidophilus* CSG in an amount from about 0.001% to about 0.1% by weight, the *Bifidobacterium longum* HY8001 in an amount from about 0.001% to about 0.1% by weight, the Alder tree extract in an amount from about 32% to about 36% by weight, the Selfheal extract in an amount from about 38% to about 42% by weight, the milk thistle extract in an amount from about 0.1% to about 0.8% by weight, the green bean-rice bran fermentation extract in an amount from about 1.0% to about 2.5% by weight, the turnip extract in an amount from about 0.1% to about 0.2% by weight, the tomato extract in an amount from about 0.8% to about 1.5% by weight, the broccoli extract in an amount from about 0.1% to about 0.5% by weight, the pineapple extract in an amount from about 0.15% to about 0.25% by weight, the colostrum powder in an amount from about 3.0% to about 4.0% by weight, the betaine in an amount from about 4.5% to about 5.0% by weight, and the composite vitamin premix in an amount from about 2.0% to about 3.0% by weight based on the total weight of the composition and water is added in an amount from about 3.85% to about 18.24% by weight, based on the total weight of the composition.

10. A health food, containing as an effective component a composition for liver function improvement, blood alcohol level reduction and in-vivo antioxidant activity enhancement, said composition comprising *Lactobacillus brevis* HY7401, *Lactobacillus fermentum* CS332, *Lactobacillus acidophilus* CSG, *Bifidobacterium longum* HY8001, an Alder tree extract, a Selfheal extract, a milk thistle extract, a green bean-rice bran fermentation extract, a turnip extract, a tomato extract, a broccoli extract, a pineapple extract, a colostrum powder, betaine, and vitamins $B_1$, $B_2$, $B_3$, $B_6$, $B_9$, $B_{12}$, C, and E.

11. The health food according to claim 10, wherein,
the *Lactobacillus brevis* HY7401 is in a form of a freeze-dried powder at a density of $10^{11}$ cfu per g,
the *Lactobacillus fermentum* CS332 is a form of a freeze-dried powder at a density of $10^{11}$ cfu per g,
the *Lactobacillus acidophilus* CSG is in a form of a freeze-dried powder at a density of $10^{11}$ cfu per g,
the *Bifidobacterium longum* HY8001 is in a form of a freeze-dried powder at a density of $10^{11}$ cfu per g,
the Alder tree extract is an extract obtained by boiling xylem and bark of dried Alder tree in water for about 1-5 hours,
the Selfheal extract is an extract obtained by boiling dried Selfheal in water for 1-5 hours,
the milk thistle extract had a total flavonoid content of about 80% to about 95% by weight and a sylibin content of about 28% to about 32% by weight,
the green bean-rice bran fermentation extract is a commercially available green bean-rice bran fermentation extract in a liquid state,
the turnip extract is in a liquid state with a Brix° of 34 to 36,
the tomato extract is an extract prepared by grinding tomato fruits together with water, filtering the mixture, and spray-drying the filtrate,
the broccoli extract is an extract prepared by grinding parboiled broccoli pieces in water, filtering the mixture, and spray-drying the filtrate,
the pineapple extract is an extract prepared by grinding pineapple slices in water, filtering the mixture, and spray-drying the filtrate,
the colostrum powder, when diluted 50,000-fold with distilled water, shows a titer of IgG specific for HAV (hepatitis A virus) in the range from about 1 to about 1.7 OD at 490 nm,
the betaine is in an anhydrous form with a purity of 9 about 9% to about 100% by weight, and
the vitamins $B_1$, $B_2$, $B_3$, $B_6$, $B_9$, $B_{12}$, C, and E are in a composite premix form.

12. The health food according to claim 11, wherein the *Lactobacillus brevis* HY7401 is contained in an amount from about 0.001% to about 0.1% by weight, the *Lactobacillus fermentum* CS332 in an amount from about 0.001% to about 0.1% by weight, the *Lactobacillus acidophilus* CSG in an amount from about 0.001% to about 0.1% by weight, the *Bifidobacterium longum* HY8001 in an amount from about 0.001% to about 0.1% by weight, the Alder tree extract in an amount from about 32% to about 36% by weight, the Selfheal extract in an amount from about 38% to about 42% by weight, the milk thistle extract in an amount from about 0.1% to about 0.8% by weight, the green bean-rice bran fermentation extract in an amount from about 1.0% to about 2.5% by weight, the turnip extract in an amount from about 0.1% to about 0.2% by weight, the tomato extract in an amount from about 0.8% to about 1.5% by weight, the broccoli extract in an amount from about 0.1% to about 0.5% by weight, the pineapple extract in an amount from about 0.15% to about 0.25% by weight, the colostrum powder in an amount from about 3.0% to about 4.0% by weight, the betaine in an amount from about 4.5% to about 5.0% by weight, and the composite vitamin premix in an amount from about 2.0% to about 3.0% by weight, based on a total weight of the composition and water is added in an amount from about 3.85% to about 18.24% by weight, based on the total weight of the composition.

* * * * *